(12) United States Patent
Kang et al.

(10) Patent No.: US 11,708,399 B2
(45) Date of Patent: *Jul. 25, 2023

(54) PHARMACEUTICAL COMPOSITION COMPRISING IMMUNOGLOBULIN FC-FUSED INTERLEUKIN-7 FUSION PROTEIN FOR PREVENTING OR TREATING HUMAN PAPILLOMAVIRUS-CAUSED DISEASES

(71) Applicant: GENEXINE, INC., Seongnam-si (KR)

(72) Inventors: Moon Cheol Kang, Pohang-si (KR); Young Woo Choi, Pohang-si (KR); Donghoon Choi, Yongin-si (KR); Young Chul Sung, Seoul (KR)

(73) Assignee: GENEXINE, INC., Seongnam-si (KR)

( * ) Notice: Subject to any disclaimer, the term of this patent is extended or adjusted under 35 U.S.C. 154(b) by 308 days.

This patent is subject to a terminal disclaimer.

(21) Appl. No.: 15/775,182

(22) PCT Filed: Dec. 2, 2016

(86) PCT No.: PCT/KR2016/014127
§ 371 (c)(1),
(2) Date: May 10, 2018

(87) PCT Pub. No.: WO2017/095191
PCT Pub. Date: Jun. 8, 2017

(65) Prior Publication Data
US 2018/0319858 A1 Nov. 8, 2018

Related U.S. Application Data

(60) Provisional application No. 62/361,170, filed on Jul. 12, 2016, provisional application No. 62/360,696, filed on Jul. 11, 2016, provisional application No. 62/263,262, filed on Dec. 4, 2015.

(51) Int. Cl.
| | | |
|---|---|---|
| *C07K 14/54* | (2006.01) | |
| *A61K 47/02* | (2006.01) | |
| *A61K 9/08* | (2006.01) | |
| *A61K 38/20* | (2006.01) | |
| *A61P 35/00* | (2006.01) | |
| *A61K 9/00* | (2006.01) | |

(52) U.S. Cl.
CPC ........ *C07K 14/5418* (2013.01); *A61K 9/0034* (2013.01); *A61K 9/08* (2013.01); *A61K 38/2046* (2013.01); *A61K 47/02* (2013.01); *A61P 35/00* (2018.01); *C07K 2319/30* (2013.01)

(58) Field of Classification Search
CPC ............ C07K 14/5418; C07K 2319/30; C07K 2319/00; A61K 38/2046
See application file for complete search history.

(56) References Cited

U.S. PATENT DOCUMENTS

| | | |
|---|---|---|
| 5,093,242 A | 3/1992 | Bachmair et al. |
| 6,153,380 A | 11/2000 | Nolan et al. |
| 7,585,947 B2 | 9/2009 | Morre et al. |
| 7,589,179 B2 | 9/2009 | Gillies et al. |
| 8,153,114 B2 | 4/2012 | Morre et al. |
| 10,208,099 B2 * | 2/2019 | Yang ........................ A61P 31/12 |
| 10,844,104 B2 * | 11/2020 | Yang ......................... A61P 7/00 |
| 2002/0127564 A1 | 9/2002 | Nolan |
| 2005/0054054 A1 | 3/2005 | Foss et al. |
| 2005/0164352 A1 * | 7/2005 | Lauder ............... A61K 38/2046 |
| | | 435/69.52 |
| 2005/0249701 A1 | 11/2005 | Morre et al. |
| 2006/0141581 A1 | 6/2006 | Gillies et al. |
| 2008/0206190 A1 | 8/2008 | Morre et al. |
| 2008/0300188 A1 * | 12/2008 | Yang ........................ A61P 37/02 |
| | | 514/7.6 |
| 2010/0196312 A1 | 8/2010 | Morre et al. |
| 2011/0243887 A1 | 10/2011 | Lauder et al. |
| 2012/0016104 A1 | 1/2012 | Morre et al. |
| 2013/0217864 A1 | 8/2013 | Cho et al. |
| 2014/0178393 A1 | 6/2014 | Andres et al. |
| 2014/0377218 A1 | 12/2014 | Morre et al. |

FOREIGN PATENT DOCUMENTS

| | | |
|---|---|---|
| EP | 0 314 415 B1 | 8/1994 |
| EP | 0 877 752 B1 | 5/2003 |
| JP | 2-501618 A | 6/1990 |
| JP | 2000-504220 A | 4/2000 |
| JP | 2001-509661 A | 7/2001 |

(Continued)

OTHER PUBLICATIONS

Choi et al. Intravaginal Fc-fused IL-7 attract DNA vaccine-induced CD8 T cell in the genital tract. Cytokine, online Sep. 2015; 76(1):80. (Year: 2015).*

Bork. Powers and Pitfalls in Sequence Analysis: The 70% Hurdle. Genome Research, 2000, 10:398-400 (Year: 2000).*

Sin et al. Interleukin 7 Can Enhance Antigen-Specific Cytotoxic-T-Lymphocyte and/or Th2-Type Immune Responses In Vivo. Clinical and Diagnostic Laboratory Immunology, Sep. 2000, p. 751-758 (Year: 2000).*

Huston et al. Vaccination to protect against infection of the female reproductive tract. Expert Rev. Clin. Immunol. 8(1), 81-94 (2012) (Year: 2012).*

(Continued)

*Primary Examiner* — Vanessa L. Ford
*Assistant Examiner* — Sandra Dillahunt
(74) *Attorney, Agent, or Firm* — Sterne, Kessler, Goldstein & Fox P.L.L.C.

(57) ABSTRACT

The present invention relates to a pharmaceutical composition comprising an immunoglobulin Fc region and an IL-7 fusion protein. Specifically, when a fusion protein comprising the immunoglobulin Fc region and IL-7 is administered to an affected area, a strong immune response is induced in the body and thus allows human papillomavirus-caused diseases to be prevented or treated.

16 Claims, 7 Drawing Sheets

Specification includes a Sequence Listing.

(56) References Cited

FOREIGN PATENT DOCUMENTS

| | | |
|---|---|---|
| JP | 2009-501543 A | 1/2009 |
| JP | 2010-531134 A | 9/2010 |
| JP | 2014-147396 A | 8/2014 |
| JP | 2015-57392 A | 3/2015 |
| KR | 10-2006-0112673 A | 11/2006 |
| KR | 10-2009-0045953 A | 5/2009 |
| KR | 10-2012-0041139 A | 4/2012 |
| KR | 10-2014-0004802 A1 | 1/2014 |
| KR | 10-2017-0066265 A | 6/2017 |
| WO | 97/27213 A1 | 7/1997 |
| WO | 2004/018681 A2 | 3/2004 |
| WO | 2005/021592 A2 | 3/2005 |
| WO | 2007/019232 A2 | 2/2007 |
| WO | 2009/101737 A1 | 8/2009 |
| WO | 2015/015516 A2 | 2/2015 |

OTHER PUBLICATIONS

Gottlieb et al. Future prospects for new vaccines against sexually transmitted infections. Curr Opin Infect Dis. Feb. 2017; 30(1): 77-86 (Year: 2017).*

Bowie et al. Deciphering the Message in Protein Sequences: Tolerance to Amino Acid Substitutions. Science, 1990, 247:1306-1310 (Year: 1990).*

Whisstock et al. Prediction of protein function from protein sequence and structure. Quarterly Reviews in Biophysics. 36(3):307-340, 2007 (Year: 2007).*

Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*

Lazar et al. Transforming Growth Factor alpha: Mutation of Aspartic Acid 47 and Leucine 48 Results in Different Biological Activities. Mol. Cell. Biol., 8:1247-1252,1988 (Year: 1988).*

Nam et al. Marked enhancement of antigen-specific T-cell responses by IL-7-fused nonlytic, but not lytic, Fc as a genetic adjuvant. Eur. J. Immunol. 2010. 40: 351-358) (Year: 2010).*

Fazeli et al. Efficacy of HPV-16 E7 Based Vaccine in a TC-1 Tumoric Animal Model of Cervical Cancer.Cell Journal (Yakhteh); 12(4):483-488) (Year: 2010).*

Nam et al. Marked enhancement of antigen-specific T-cell responses by II-7 fused nonlytic, but not lytic, Fc as a genetic adjuvant. Eur. J. Immunol. 2010. 40: 351-358 (Year: 2010).*

Hyo Jung Nam et al., "Marked enhancement of antigen-specific T-cell responses by IL-7-fused nonlytic, but not lytic, Fc as a genetic adjuvant," European Journal of Immunology, 2010, pp. 351-358, vol. 40.

Yong Bok Seo et al., "Crucial Roles of Interleukin-7 in the Development of T Follicular Helper Cells and in the Induction of Humoral Immunity," Journal of Virology, Aug. 2014, pp. 8998-9009, vol. 88, No. 16.

International Search Report of PCT/KR2016/014127 dated Mar. 9, 2017.

Kroncke et al.; "Human follicular dendritic cells and vascular cells produce interleukin-7: a potential Yole for interleukin-7 in the germinal center reaction"; Eur. J. Immunol. 1996. 26: 2541-2544.

Marc Pellegrini et al.; "IL-7 Engages Multiple Mechanisms to Overcome Chronic Viral Infection and Limit Organ Pathology"; Cell 144, 601-613, Feb. 18, 2011.

Miyakama et al., "Molecular cloning and functional expression of a cDNA encoding glycosylation-inhibiting factor", Proc. Natl. Acad. Sci. USA, vol. 90, pp. 10056-10060, 1993 (6 pages total).

Moon Cheol Kang, et al., "Intranasal Introduction of Fc-Fused Interleukin-7 Provides Long-Lasting Prophylaxis against Lethal Influenza Virus Infection", Journal of Virology, Mar. 2016, pp. 2273-2284, vol. 90, No. 5.

Muegge et al.; "Interleukin-7: A Cofactor for V(D)J Rearrangement of the T Cell Receptor ß Gene" Science; vol. 261; Jul. 2, 1993; pp. 93-95.

Nanjappa et al.; "Immunotherapeutic effects of IL-7 during a chronic viral infection in mice"; Blood, May 12, 2011 vol. 117, No. 19; pp. 5123-5132.

NCBI, PDB: 4C54_A (Feb. 5, 2014), "Chain A, Crystal Structure of Recombinant Human Igg4 Fc".

Patel et al.; "Treatment of progressive multifocal leukoencephalopathy and idiopathic CD4+ lymphocytopenia"; J Antimicrob Chemother 2010; 65: 2489-2492; publication Oct. 20, 2010.

Pellegrini et al.; "Adjuvant IL-7 antagonizes multiple cellular and molecular inhibitory networks to enhance immunotherapies"; nature medicine; vol. 15; No. 5; May 2009; pp. 528-536, 819.

Rosenberg et al.; "IL-7 Administration to Humans Leads to Expansion of CD8+ and CD4+ Cells but a Relative Decrease of CD4+ T-Regulatory Cells"; National Institute of Health; NIH Public Access Author Manuscript; J Immunother: 2006; 29(3): 313-319.

Sawa et al.; "Hepatic Interleukin-7 Expression Regulates T Cell Responses"; Immunity 30, 447-457, Mar. 20, 2009.

Snyder et al.; "IL-7 in allogeneic transplant: Clinical promise and potential pitfalls"; Leukemia & Lymphoma, Jul. 2006; 47(7): 1222-1228.

Voet et al., Biochemistry John Wiley & Sons Inc. (1990), pp. 126-128 and 228-234 (12 pages total).

Watanabe et al.; "Interleukin 7 Is Produced by Human Intestinal Epithelial Cells and Regulates the Proliferation of Intestinal Mucosal Lymphocytes"; J. Clin. Invest. vol. 95, Jun. 1995, pp. 2945-2953.

European Patent Office; Communication dated May 15, 2019 in application No. 16807859.0.

European Patent Office; Search Report dated Dec. 19, 2018 issued in application No. 16 807 859.0.

Fry et al.; "Interleukin-7: from bench to clinic"; Blood, Jun. 1, 2002 vol. 99, No. 11; pp. 3892-3904.

GenBank, "interleukin-7 [synthetic construct]", Accession No. AAB70834.1 (Sep. 21, 1997), total 1 page.

Heufler et al.; "Interleukin 7 Is Produced by Murine and Human Keratinocytes"; J. Exp. Med.; The Rockefeller University Press; vol. 178; Sep. 1993; pp. 1109-1114.

International Preliminary Report on Patentability and Written Opinion of the International Searching Authority dated Dec. 12, 2017 for related PCT/KR2016/006214.

International Search Report for PCT/KR2016/006214 dated Aug. 24, 2016.

International Search Report for PCT/KR2016/013966 dated Mar. 2, 2017 [PCT/ISA/210].

International Search Report of PCT/KR2016/012495 dated Jan. 13, 2017.

Japanese Patent Office; Search Report dated Jan. 8, 2019 issued in application No. 2017-564121.

Bork, "Powers and Pitfalls in Sequence Analysis: The 70% Hurdle", Genome Research, vol. 10, pp. 398-400, 2000 (4 pages total).

Greenspan et al., "Defining epitopes: It's not as easy as it seems", Nature Biotechnology, 1999, vol. 17, pp. 936-937 (2 pages total).

* cited by examiner

1: Liver, 2: Heart, 3: Lung, 4: Spleen, 5: Kidney
6: Rectum, 7: Cervix-vagina; 8: Uterus, 9: Ovary

PHARMACEUTICAL COMPOSITION COMPRISING IMMUNOGLOBULIN FC-FUSED INTERLEUKIN-7 FUSION PROTEIN FOR PREVENTING OR TREATING HUMAN PAPILLOMAVIRUS-CAUSED DISEASES

CROSS REFERENCE TO RELATED APPLICATIONS

This application is a National Stage of International Application No. PCT/KR2016/014127 filed Dec. 2, 2016, claiming priority based on U.S. Patent Application No. 62/263,262 filed Dec. 4, 2015, U.S. Patent Application No. 62/360,696 filed Jul. 11, 2016, and U.S. Patent Application No. 62/361,170 filed Jul. 12, 2016.

TECHNICAL FIELD

The present invention relates to a composition of a fusion protein comprising interleukin-7 for preventing or treating a human papillomavirus-derived disease.

BACKGROUND ART

Interleukin-7 (hereinafter 'IL-7') is an immune-stimulating cytokine that stimulates immune responses mediated by B cell and T cell, and plays an important role in the adaptive immune system. IL-7 is mainly secreted from stromal cells of bone marrow and thymus, but also produced in keratinocytes, dendritic cells, hepatocytes, nerve cells, and epithelial cells (Heufler C et al., 1993, *J. Exp. Med.* 178 (3)): 1109-14).

Specifically, interleukin-7 activates immune function through stimulation of the survival and differentiation of T cells and B cells, the survival of lymphoid cells, and the activation of NK (natural killer) cells, and is especially important for the development of T cells and B cells. It is bound with HGF (hepatocyte growth factor) and functions as pre-pro-B cell growth-stimulating factor or a cofactor for V(D)J rearrangement of T cell receptor beta (TCRβ) (Muegge K, 1993, Science 261 (5117): 93-5). In addition, interleukin-7 regulates lymph node development through lymphoid tissue inducer (LTi) cells and promotes the expansion and survival of naive T cells or memory T cells. It is also known that IL-7 stimulates the secretion of IL-2 and interferon-gamma (interferon-γ), thereby enhancing the human immune response.

Meanwhile, papillomavirus is a DNA-based virus with a diameter of 52 to 55 nm, which infects skin and subcutaneous tissue of humans and other animals. Human papillomavirus (HPV) is usually transmitted through skin keratinocytes or mucous membranes. More than 100 human papillomaviruses (HPV) have been found so far, most of which do not show any symptoms, but in some cases they can cause papillomas in humans. Some HPVs cause the development of warts, and some cause precancerous lesions. In particular, high-risk viruses such as human papilloma virus 16 (HPV 16) and human papilloma virus 18 (HPV 18) can cause cancer such as cervical cancer and testicular cancer.

Cervical cancer is one of the most common causes of cancer-related deaths in women worldwide. Almost all of the cases are caused by infection with human papillomavirus (HPV). Among them, HPV16 and HPV18 account for about 70-75% of cervical cancer patients. Continuous proliferation of infected cells leads to a pre-malignant cervical intraepithelial neoplasia (CIN), which then gradually transform into invasive cancer.

While the prophylactic HPV vaccines can efficiently prevent HPV infection, they do not have therapeutic effects against pre-existing infection and HPV-induced lesions. The most common treatment for CIN2 and CIN3 is surgical excision, which is associated with pregnancy-related complications and a 10% recurrence rate. More seriously, the mortality rate of cervical cancer after conventional treatment is more than 50%.

Meanwhile, recently, therapies to treat HPV infection have been developed by inducing immune enhancement. It has been reported that local administration of toll-like receptor (TLR) agent 7 and 9, imiquimod and CpG after administration of vaccine including HPV16 E7 antigen induced accumulation of E7-specific CD8 T cells in the genital tract and regression of genital tumors (Soong R-S et al., 2014, *Clin. Cancer Res.* 20:5456-67). However, in humans, imiquimod usage can induce side effects such as acute and severe local inflammation and ulceration, and administration of CpG requires repeated injections due to its short-lived efficacy. The ability of cytokines, such as IL-2 and IL-15, which function as vaccine adjuvants in animal models, were studied in order to enhance the therapeutic efficacy (Abraham E et al., 1992, *J Immunol* 149:3719-26). However, such cytokines also require repeated injections and may induce adverse effects, e.g., capillary leakage syndrome in case of IL-2.

Therefore, there still exists a need to develop effective and non-surgical therapy for the prevention and treatment of diseases caused by HPV infection.

DISCLOSURE OF INVENTION

Technical Problem

The object of the present invention is to provide a composition for preventing or treating a human papillomavirus-derived disease.

Another object of the present invention is to provide a method for preventing or treating a human papillomavirus-derived disease.

Solution to Problem

In accordance with one aspect of the present invention, there is provided a pharmaceutical composition comprising a fusion protein of immunoglobulin Fc region and IL-7. Also, there is provided a method for preventing or treating a human papillomavirus-derived disease by mucosal administration of the pharmaceutical composition comprising the fusion protein.

Advantageous Effects of Invention

In case where a fusion protein comprising immunoglobulin Fc region and IL-7 according to the present invention is administered via a mucosal route, the number of antigen-specific T cells is increased to prevent or treat a human papillomavirus-derived disease. Also, such administration is easy to conduct. Therefore, the fusion protein comprising immunoglobulin Fc region and IL-7 according to the present invention can be utilized as a new pharmaceutical composition which can replace the conventional HPV preventive vaccine.

BEST MODE FOR CARRYING OUT THE INVENTION

Figure 1:
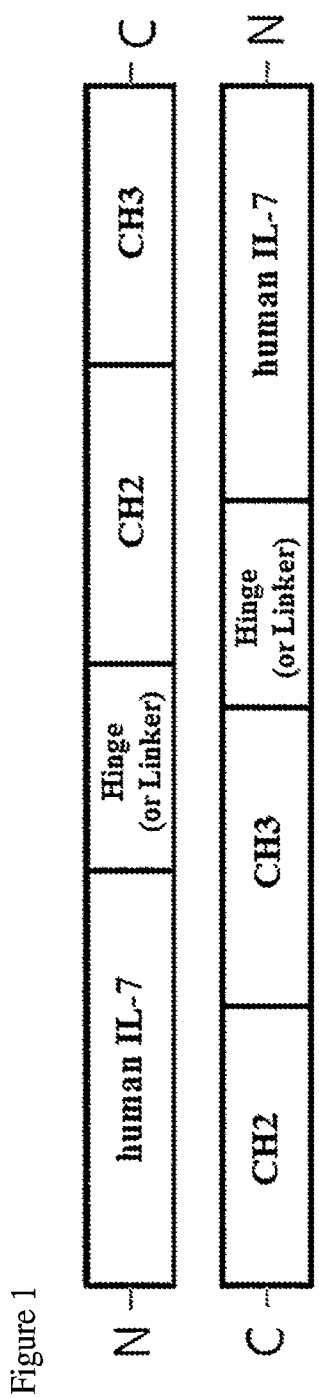
FIG. 1 is a schematic illustration of the structure of IL-7 fused with Fc.

Hereinafter, the present invention is explained in detail.

In one aspect for achieving the object, the present invention provides a pharmaceutical composition for preventing or treating a genital disease comprising an interleukin-7 (IL-7) fusion protein in which immunoglobulin Fc region is fused.

The genital disease may be a human papillomavirus-derived disease.

As used herein, the term "human papillomavirus-derived disease" or "human papillomavirus infection disease" refers to a disease caused by human papilloma virus (HPV) infection. Human papilloma virus-derived diseases can be classified into CIN1, CIN2, CIN3, LSIL (low grade squamous intraepithelial lesion), HSIL (high grade squamous intraepithelial lesion) or cancer, etc., depending on the degree of infection or status of a lesion.

As used herein, the term "interleukin-7" may be a protein having the same amino acid sequence as interleukin-7 derived from an animal or a human. Further, the term "interleukin-7" may be a polypeptide or a protein having an activity similar to the interleukin-7 derived in vivo. Specifically, the IL-7 may be a protein comprising an IL-7 protein or a fragment thereof. Also, the IL-7 may be derived from a human, a rat, a mouse, a monkey, cattle or sheep.

The IL-7 comprises a polypeptide consisting of the amino acid sequences represented by SEQ ID NO: 1 to SEQ ID NO: 6. In addition, the IL-7 may have homology of about 70%, 75%, 80%, 85%, 90%, 91%, 92%, 93%, 94%, 95%, 96%, 97%, 98%, 99% or more to the sequences of SEQ ID NO: 1 to SEQ ID NO: 6.

Specifically, human IL-7 may have an amino acid sequence represented by SEQ ID NO: 1 (Genbank Accession No. P13232); rat IL-7 may have an amino acid sequence represented by SEQ ID NO: 2 (Genbank Accession No. P56478); mouse IL-7 may have an amino acid sequence represented by SEQ ID NO: 3 (Genbank Accession No. P10168); monkey IL-7 may have an amino acid sequence represented by SEQ ID NO: 4 (Genbank Accession No. NP_001279008); bovine IL-7 may have an amino acid sequence represented by SEQ ID NO: 5 (Genbank Accession No. P26895); and sheep IL-7 may have an amino acid sequence represented by SEQ ID NO: 6 (Genbank Accession No. Q28540).

In addition, the IL-7 protein or a fragment thereof may comprise a variety of modified proteins or peptides, i.e., variants. Such modification may be carried out by substitution, deletion or addition of one or more proteins of wild-type IL-7, which does not alter the function of IL-7. These various proteins or peptides may have homology of 70%, 75%, 80%, 85%, 90%, 91%, 92%, 93%, 94%, 95%, 96%, 97%, 98%, or 99% to a wild-type protein.

In general, substitution of a wild-type amino acid residue can be accomplished by substituting alanine or a conservative amino acid that does not affect the charge, polarity, or hydrophobicity of the entire protein.

The term "IL-7 protein" as used in the specification may be used as a concept including "IL-7 protein" and a fragment thereof. The terms "protein," "polypeptide," and "peptide" may be used interchangeably, unless otherwise specified.

In addition, the IL-7 may be a modified IL-7 having the following structure:

A-IL-7, wherein said A is an oligopeptide consisting of 1 to 10 amino acid residues, and the IL-7 is an interleukin-7 or a polypeptide having the activity similar to the interleukin-7.

Herein, said A may be directly linked to the N-terminus of the IL-7 or may be linked through a linker.

Said A may increase the productivity of IL-7 and may be prepared according to the method disclosed in Korean Patent Application No. 10-2016-0072769.

As used herein, said A may be linked to the N-terminus of IL-7. In the above formula, said A is characterized by containing 1 to 10 amino acids, which may be preferably selected from the group consisting of methionine, glycine, serine, and a combination thereof.

It is known that methionine and glycine do not induce an immune response in the human body. Although various protein therapeutic agents produced from E. coli necessarily contain methionine at the N-terminus thereof, no adverse immune effect has been reported. In the meantime, glycine is widely used in GS linker, and it is known that a commercial product such as Dulaglutide does not induce an immune response.

According to one embodiment, the oligopeptide A may be an oligopeptide comprising 1 to 10 amino acids selected from the group consisting of methionine (Met, M), glycine (Gly, G) and a combination thereof. Preferably, the oligopeptide A may be an oligopeptide consisting of 1 to 5 amino acids. For example, the oligopeptide A may be represented by the amino acid sequence selected from the group consisting of methionine, glycine, methioninemethionine, glycine-glycine, methionine-glycine, glycine-methionine, methioninemethionine-methionine, methionine-methionine-glycine, methionine-glycinemethionine, glycine-methionine-methionine, methionine-glycine-glycine, glycinemethionine-glycine, glycine-glycine-methionine, and glycine-glycine-5 glycine. Herein, the modified IL-7 may have any one of the amino acid sequences selected from SEQ ID NOS: 15 to 20.

Further, immunoglobulin Fc region may comprise an animal or human immunoglobulin Fc region, or a modified immunoglobulin Fc region thereof.

The IL-7 may be linked to the N-terminus or the C-terminus of the Fc region. It is known that even when IL-7 is fused to the C-terminus of the Fc region, IL-7 activity is maintained (U.S. Pat. No. 8,338,575 B2). Herein, the IL-7 may be linked to Fc region through a linker.

As used herein, the term "Fc region," "Fc fragment" or "Fc" refers to a protein which comprises heavy chain constant region 2 (CH2) and heavy chain constant region 3 (CH3) of immunoglobulin but does not comprise variable regions of heavy or light chain and light chain constant region 1 (CL1). It may further comprise a hinge region of the heavy chain constant region. Hybrid Fc or a hybrid Fc fragment may herein also be referred to as "hFc" or "hyFc." Also, as used herein, the term "a modified immunoglobulin Fc region" or "Fc region variant" refers to a Fc region in which one or more amino acids in the Fc region are substituted or a Fc region which is prepared by combining different Fc regions. Preferably, it refers to a Fc region whose binding force with a Fc receptor and/or a complement has been modified so as to exhibit weakened antibody-dependent cell-mediated cytotoxicity (ADCC) or complement dependent cytotoxicity (CDC) compared to the wild-type Fc region. The modified immunoglobulin Fc region may be a combination sequence of two or more of IgG1, IgG2, IgG3, IgD, and IgG4.

In particular, the modified immunoglobulin Fc region comprises CH2 domain and CH3 domain in the N-terminus to C-terminus direction, wherein the CH2 domain comprises a portion of an amino acid residue of CH2 domain of human IgD and human IgG4, and the CH3 domain comprises a portion of an amino acid residue of human IgG4 CH3 domain.

The Fc region variant can be modified so as to prevent the cleavage at the hinge region. Specifically, the $144^{th}$ amino acid and/or the $145^{th}$ amino acid of SEQ ID NO: 9 can be modified. Preferably, the variant may be a mutant in which K, the $144^{th}$ amino acid of SEQ ID NO: 9, is substituted by G or S, and E, the $145^{th}$ amino acid, is substituted by G or S.

In particular, the Fc region of the modified immunoglobulin comprises CH2 domain and CH3 domain in the N-terminus to C-terminus direction, wherein the CH2 domain comprises a portion of an amino acid residue of CH2 domain of human IgD and human IgG4, and the CH3 domain comprises a portion of an amino acid residue of human IgG4 CH3 domain.

As used herein, the term "Fc region", "Fc fragment" or "Fc" refers to a protein which comprises heavy chain constant region 2 (CH2) and heavy chain constant region 3 (CH3) of immunoglobulin but does not comprise variable regions of heavy or light chain light chain and constant region 1 (CL1). It may further comprise a hinge region of the heavy chain constant region. Hybrid Fc or a hybrid Fc fragment may herein also be referred to as "hFc" or "hyFc". Also, as used herein, the term "Fc region variant" refers to a Fc region in which one or more amino acids in the Fc region are substituted or which is produced by combining different Fc regions. The Fc region variant can be modified so as to prevent severing at the hinge region. Specifically, the 144th amino acid and/or the 145th amino acid of SEQ ID NO: 9 can be modified. Preferably, the variant may be a mutant in which K, the 144th amino acid of SEQ ID NO: 9, is substituted by G or S, and E, the 145th amino acid, is substituted by G or S.

In addition, the hFc can be represented by the following formula (I):

$$\text{N'-(Z1)}p\text{-(Y)}q\text{-Z2-Z3-Z4-C'}, \quad \text{[Formula (I)]}$$

wherein,

N' is the N-terminus of a polypeptide and C' is the C-terminus of the polypeptide, p or q is an integer of 0 or 1, Z1 is an amino acid sequence having 5 to 9 consecutive amino acid residues in the N-terminus direction from the $98^{th}$ position in the amino acid residues at $90^{th}$ to $98^{th}$ positions of SEQ ID NO: 7, Y is an amino acid sequence having 5 to 64 consecutive amino acid residues in the N-terminus direction from the $162^{nd}$ position in the amino acid residues at $99^{th}$ to $162^{nd}$ positions of SEQ ID NO: 7, Z2 is an amino acid sequence having 4 to 37 consecutive amino acid residues in the C-terminus direction from the $163^{rd}$ position in the amino acid residue at positions $163^{rd}$ to $199^{th}$ in SEQ ID NO: 7, Z3 is an amino acid sequence having 70 to 106 consecutive amino acid residues in the N-terminus direction from the $220^{th}$ position in the amino acid residues at $115^{th}$ to $220^{th}$ positions of SEQ ID NO: 8, and Z4 is an amino acid sequence having 80 to 107 consecutive amino acid residues in the C-terminus direction from the $221^{th}$ position in the amino acid residues at $221^{st}$ to $327^{th}$ positions of SEQ ID NO: 8.

In addition, the modified immunoglobulin Fc region or Fc region variant can be represented by the following formula (II):

$$\text{N'-(Z1)}p\text{-Y-Z2-Z3-Z4-C'}, \quad \text{[Formula (II)]}$$

wherein,

N' is the N-terminus of a polypeptide and C' is the C-terminus of the polypeptide, p is an integer of 0 or 1, Z1 is an amino acid sequence having 5 to 9 consecutive amino acid residues in the N-terminus direction from the $98^{th}$ position in the amino acid residues at $90^{th}$ to $98^{th}$ positions of SEQ ID NO: 7, Y is an amino acid sequence having 5 to 64 consecutive amino acid residues in the N-terminus direction from the $162^{nd}$ position in the amino acid residues at $99^{th}$ to $162^{nd}$ positions of SEQ ID NO: 7, Z2 is an amino acid sequence having 4 to 37 consecutive amino acid residues in the C-terminus direction from the $163^{rd}$ position in the amino acid residue at positions $163^{rd}$ to $199^{th}$ in SEQ ID NO: 7, Z3 is an amino acid sequence having 70 to 106 consecutive amino acid residues in the N-terminus direction from the $220^{th}$ position in the amino acid residues at $115^{th}$ to $220^{th}$ positions of SEQ ID NO: 8, and Z4 is an amino acid sequence having 80 to 107 consecutive amino acid residues in the C-terminus direction from the $221^{st}$ position in the amino acid residues at $221^{st}$ to $327^{th}$ positions of SEQ ID NO: 8.

In addition, Fc fragment of the present invention may be a wild type sugar chain, an increased sugar chain compared with the wild type, a reduced sugar chain compared with the wild type, or a form in which the sugar chain is removed. The increase, reduction or removal of immunoglobulin Fc sugar chain can be carried out by a conventional method known in the art such as chemical method, enzymatic method and genetic engineering method using microorganisms. The removal of the sugar chain from Fc fragment rapidly reduces the binding affinity of the primary complement component C1 to C1q and results in a decrease or loss of ADCC (antibody-dependent cell-mediated cytotoxicity) or CDC (complement-dependent cytotoxicity), thereby not inducing unnecessary immune responses in vivo. In this regard, immunoglobulin Fc fragment in a deglycosylated or aglycosylated form may be more suitable for the purpose of the present invention as a carrier of a drug. As used herein, the term "deglycosylation" refers to enzymatical elimination of sugar from Fc fragment, and the term "aglycosylation" refers to the production of Fc fragment in an unglycosylated form by a prokaryote, preferably *E. coli*.

The modified immunoglobulin Fc region may comprise amino acid sequences of SEQ ID NO: 9 (hFc01), SEQ ID NO: 10 (hFc02), SEQ ID NO: 11 (hFc03), SEQ ID NO: 12 (hFc04) or SEQ ID NO: 13 (hFc05). In addition, the modified immunoglobulin Fc region may comprise the non-lytic mouse Fc of SEQ ID NO: 14.

According to the present invention, the modified immunoglobulin Fc region may be one described in U.S. Pat. No. 7,867,491, and the production of the modified immunoglobulin Fc region may be carried out with reference to the disclosure of U.S. Pat. No. 7,867,491.

In addition, the interleukin-7 fusion protein in which immunoglobulin Fc region is fused may have the amino acid sequence of any one of SEQ ID NOS: 21 to 27.

Meanwhile, the interleukin-7 fusion protein in which immunoglobulin Fc region is fused according to the present invention may further comprise a pharmaceutically acceptable carrier. The pharmaceutically acceptable carrier may be any carrier that is suitable for being delivered to a patient and is non-toxic to the patient. Distilled water, alcohol, fats, waxes and inert solids may be included as carriers. Pharmacologically acceptable adjuvant (a buffer or a dispersant) may also be included in the pharmacological composition.

In another aspect of the present invention, there is provided a method for preventing or treating a genital disease comprising administering to an individual an interleukin-7 (IL-7) fusion protein in which immunoglobulin Fc region is fused and a pharmaceutically acceptable carrier.

The genital disease may be a human papillomavirus-derived disease, for example, cervical cancer.

Herein, the method of administration to an individual may be a local administration, preferably mucosal administration. In case of that the composition of the present invention is provided topically, such as intravaginal or aerosol administration, the composition preferably comprises a portion of an aqueous or physiologically compatible body fluid suspension or solution. Accordingly, the carrier or vehicle may be physiologically acceptable, and thus it can be added to the composition and delivered to the patient, which does not adversely affect the electrolyte and/or volume balance of the patient. Thus, a carrier for a formulation may generally include physiologic saline. Also, it may include a portion of viscous suspension or solution depending on the lesion or physiological condition.

The method for preventing or treating a disease using a fusion protein of the present invention or a composition comprising the same may comprise administering another drug or physiologically active substance having the effect of preventing or treating a disease in combination with the protein or the composition of the present invention, while the route, timing, and dosage of the administration may be determined depending on the type of a disease, the disease condition of a patient, the purpose of treatment or prevention, and other drugs or physiologically active substances co-administered.

The isolated nucleic acid molecule encoding the modified interleukin-7 or a fusion protein comprising the same may encode a polypeptide having an amino acid sequence selected from the group consisting of SEQ ID NOS: 15 to 25. The nucleic acid molecule may comprise a polynucleotide sequence selected from the group consisting of SEQ ID NOS: 29 to 39. The nucleic acid molecule may further comprise a signal sequence or a leader sequence.

MODE FOR THE INVENTION

Hereinafter, the present invention is explained in detail. The following Examples are intended to further illustrate the present invention without limiting its scope.

Preparation Example 1: Preparation of Experimental Animals

Female C57BL/6 mice, 8-10 weeks of age used in the following examples were purchased from The Jackson Laboratory (Bar Harbor, USA). All animals were raised under specific pathogen-free conditions in the animal care facility in POSTECH. The procedures of animal experiments were performed in accordance with the National Institutes of Health (NIH) guidelines for mouse experiments. The protocol was approved by the Institutional Animal Care and Use Committee (IACUC). Also, female Sprague-Dawley rats at 11 weeks of age were purchased from the Charles River Laboratories (Raleigh, USA). All animals were raised under specific pathogen-free conditions in the animal care facility of MPI research. The procedures of animal experiments were performed in accordance with the regulations outlined in the United States Department of Agriculture (USDA) animal welfare act (9 CFR, parts 1-3).

Preparation Example 2: Preparation and Treatment of Fusion Protein of Fc and IL-7

The codon-optimized human IL-7 and granulocyte colony-stimulating factor (G-CSF) genes were individually fused with a hybrid Fc-fragment. The schematic structure of Fc-fused IL-7 is shown in FIG. 1. Chinese hamster ovary (CHO) cells were stably transfected with a plasmid encoding IL-7-Fc and G-CSF-Fc. And then, IL-7-Fc and G-CSF-Fc were obtained from the cells. Purified recombinant human IL-7 (rIL-7), for a control group, was purchased from Biolegend (San Diego, USA).

3 mg of medroxyprogesterone acetate (Depo-Provera, Pfizer) was subcutaneously injected to mice in a diestrus state 4 days before treatment. The mice were anesthetized by intraperitoneal injection with 100 mg/kg ketamine (Yuhan) and 10 mg/kg xylazine hydrochloride (Bayer) in PBS. Then, 10 μg of rIL-7, IL-7-Fc or G-CSF-Fc were mixed with PBS and applied (administered) on the vaginal mucosal tissues using a micropipette.

Preparation Example 3: Identification of Fluorescence-Conjugated IL-7-Fc in the Genital Tract IL-7-Fc was coupled with Cy-5.5 mono-reactive NHS ester. Eluted proteins were desalted and concentrated by using centrifugal filter devices (Merck Millipore) and protein concentration of the dye-labeled IL-7-Fc was measured using an anti-human IL-7 ELISA set (Southern Biotech). Cy-5.5-conjugated IL-7-Fc (1 mg/kg) and Cy-5.5 in PBS were intravaginally administered to anesthetized mice with equivalent signal intensity. At days 1 and 7 after administration, mice were euthanized and their vaginas were washed, and each of the organs was obtained. The fluorescence signal intensity was then quantified using an IVIS spectral machine (Caliper Life Science). Signal intensity was measured quantitatively in the organ by measuring photons per second per centimeter squared per steradian (p/s/cm²/sr).

Preparation Example 4: Quantification of Serum IL-7

Blood samples were collected before administration and up to 7 days after administration of IL-7-Fc, and serum IL-7 concentration was measured using a human IL-7 ELISA set (Southern biotech).

Preparation Example 5: Toxicity Studies Depending on Repeated Administration After topical administration of IL-7-Fc, for histopathological analysis using a microscope, 0.8, 3 and 8 mg/kg/dose of IL-7-Fc were intravaginally administered to rats once a week for 4 weeks (total dose of 5). The uterine cervix/vaginal tissues were excised and fixed with neutralizing formalin. The fixed tissues were placed in paraffin, cut with a thickness of 4-6 μm and stained with hematoxylin and eosin (H&E, Sigma-Aldrich). To determine the dose-dependence of vaginal inflammation, rats were observed individually at 4 hours and 24 hours after each dose administration and weekly. The following scoring scale was used: 0=no erythema, 1=very slight erythema (barely perceptible), 2=well-defined erythema, 3=moderate erythema, 4=severe erythema (redness) to eschar formation.

Preparation Example 6: Splenocytes and Cervix/Vagina (CV) Cell Isolation

Spleen and CV tissues were surgically excised using sterile technique. The splenocytes were obtained by mechanically disrupting the tissues. For the preparation of CV cells, CV tissues were minced and treated with 1 mg/ml collagenase D (Roche) and 0.5 mg/ml DNase (Sigma-Aldrich). The cells were passed through a 40-μm strainer (BD), washed, and re-suspended with RPMI-1640 containing 10% FBS and antibiotics.

Preparation Example 7: Flow Cytometry

To prevent non-specific binding of immunoglobulins to Fc receptor, the cells used in the following Examples were treated with CD16/32 (2.4G2) and stained with the following monoclonal antibodies: CD4 (RM4-5), CD8 (53-6.7), CD44 (IM7), CD62L (MEL-14), CD11b (M1/70), CD11c (N418), and MHCII (M5/114.15.2), from eBioscience; CD3e (145-2C1), and TCRγδ (GL3), from BD; CXCR3 (CXCR3-173), from Biolegend; and Live/Dead (Life technologies). All samples were analyzed using an LSR Fortessa (BD) and FlowJo software (Tree Star).

Preparation Example 8: Statistical Analysis

A two-tailed paired Student's t-test was used to evaluate the statistical difference between the two experimental groups. For in vivo tumor experiments, differences in survival rates between the groups were determined by a log-rank test using the Prism 5.0 software (GraphPad).

Example 1: Assessment of Administration Method of IL-7-Fc Fusion Protein

Cy-5.5 (Cy-5.5) and Cy-5.5-conjugated IL-7-Fc (Cy5.5-IL-7-Fc) were intravaginally administered to C57BL/6 wild-type mice (n=3/group). The results are shown in FIGS. 2a and 2b.

Figure 2A:
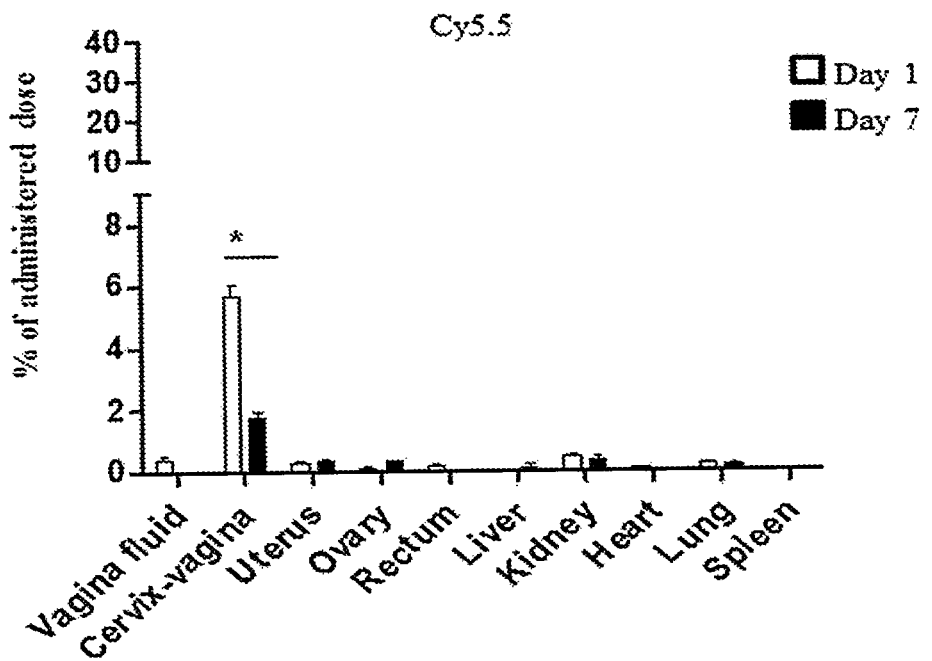
FIGS. 2a and 2b are bar graphs and fluorescence images, respectively, which show fluorescence intensities in various organs on days 1 and 7 after administration of Cy5.5 and IL-7-Fc-Cy5.5 to the mucous membrane, respectively (*, $p<0.05$).
Figure 2A:
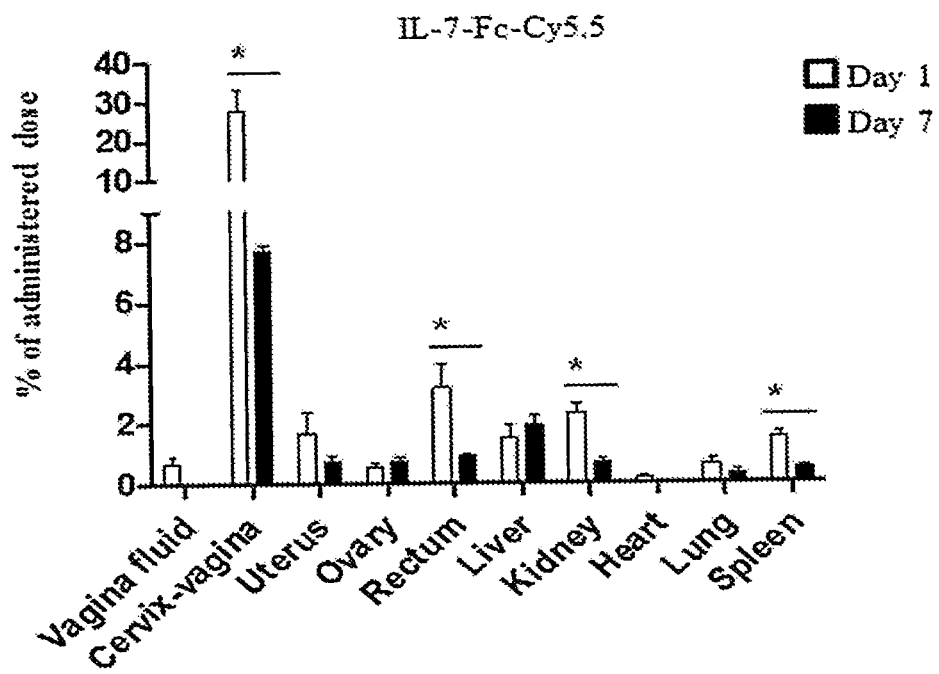
Figure 2B:
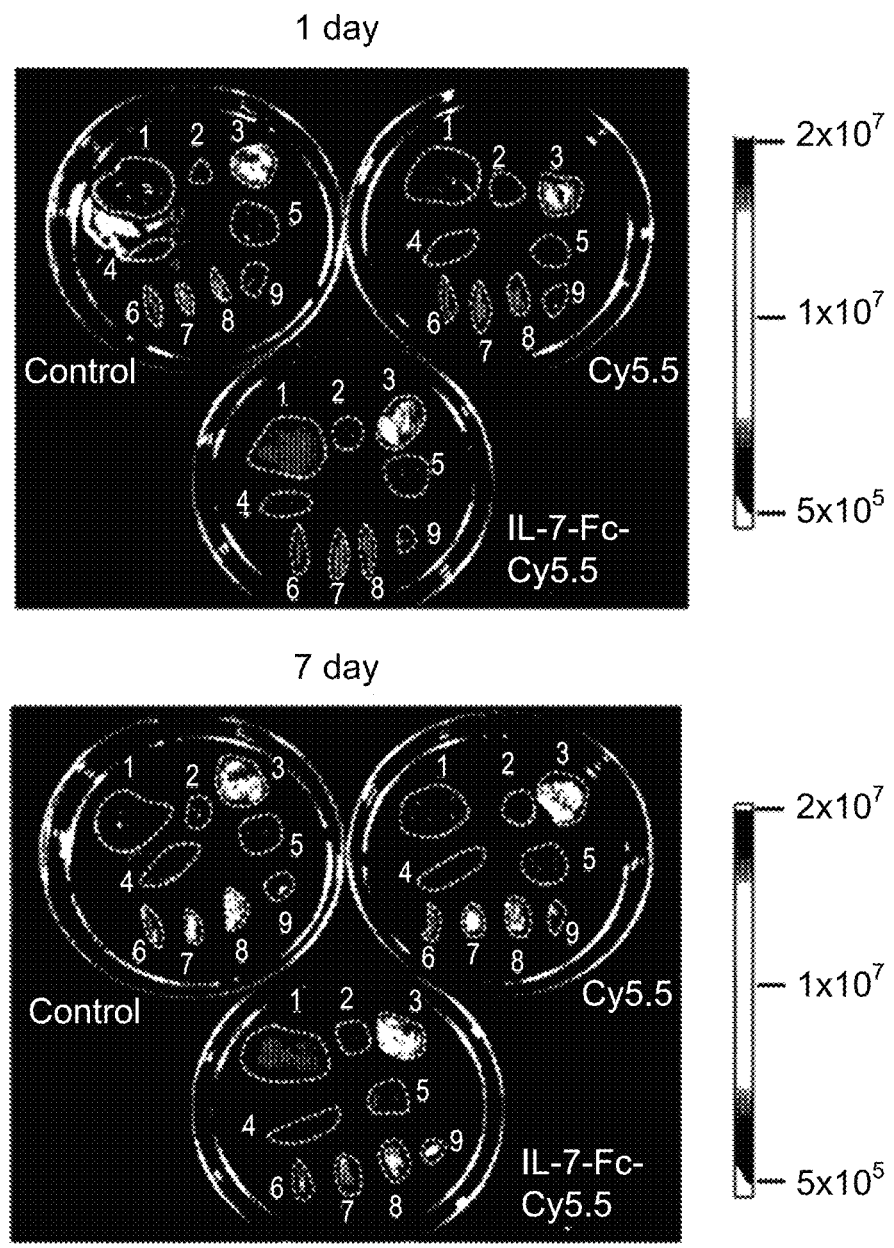

As shown in FIGS. 2a and 2b, the intensity of Cy-5.5-IL-7-Fc in the cervix/vagina (CV) tissues increased significantly at 1 day post-administration and observed for 7 days. In particular, signal intensities in CV tissues of Cy5.5-IL-7-Fc-treated mice were 6 and 4.5 times higher than the control (Cy5.5 treated mice) at days 1 and 7 after administration, respectively. Fluorescence signals were also detected at high intensities in various cervix/vagina adjacent tissues (cervix-vagina, uterus, ovary, and rectum) of Cy5.5-IL-7-Fc-treated mice. In particular, mice treated with Cy5.5-IL-7-Fc maintained high levels of fluorescence not only in the genital tract tissues but also in the liver, kidney and spleen even at day 7.

Figure 3:
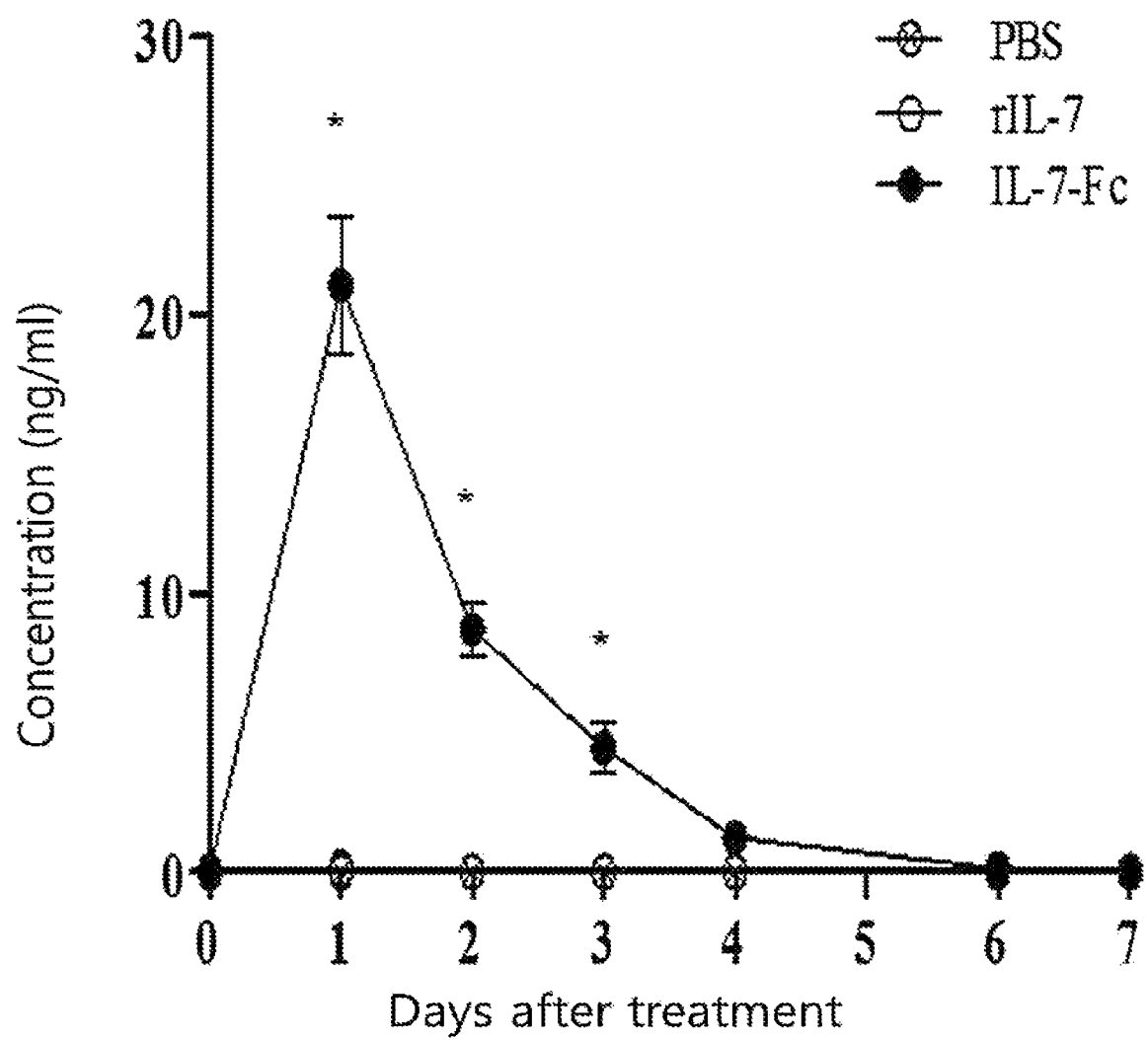
FIG. 3 illustrates that IL-7-Fc is transported to serum through FcRn-mediated transcytosis after administration of PBS, rIL-7, and IL-7-Fc to the mice intravaginally (*, $p<0.05$ (rIL-7 vs IL-7-Fc)).

Example 2: Confirmation of Systemic Circulation of Intravaginally Administered IL-7-Fc PBS, rIL-7 and IL-7-Fc were intravaginally administered to mice (n=7/group), and serum concentration of IL-7 was measured by human IL-7 ELISA. The results are shown in FIG. 3. As shown in FIG. 3, mice treated with IL-7-Fc, but not rIL-7, showed significantly increased levels of IL-7 as compared to PBS control.

These results reveal that the application of the Fc-fused protein on the mucosal epithelium enables genital-epithelial barrier transcytosis.

Example 3: Analysis of Changes in Leukocyte Number in Cervical Tissues after Local Administration of IL-7-Fc IL-7-Fc was intravaginally administered to mice (n=3/group) at 0, 3, 7, 14 and 21 days prior to sacrifice, and the number of leukocytes in cervical tissues was calculated using flow cytometry (Table 1). In addition, mice (n=6/group) were treated with PBS, IL-7, IL-7-Fc, IFN-α2a-Fc or G-CSF-Fc, and 7 days later, CD4 and CD8 T cells in CV tissues were analyzed by flow cytometry. The results are shown in Tables 1 and 2 and FIG. 4. The data in the table below are shown as means±SEMs (*, $p<0.05$).

TABLE 1

| | Absolute cell number after IL-7-Fc treatment | | | | |
|---|---|---|---|---|---|
| | Day 0 | Day 3 | Day 7 | Day 14 | Day 21 |
| Total CD4 T cells (×10³) | 2.86 ± 0.49 | 12.76 ± 0.53* | 51.51 ± 9.18* | 3.33 ± 0.77 | 2.57 ± 0.44 |
| CD62L$^{lo}$ CD44$^{high}$ CD4 T cells (×10³) | 2.21 ± 0.31 | 10.26 ± 0.68* | 35.06 ± 7.03* | 2.51 ± 0.72 | 2.13 ± 0.41 |
| Total CD8 T cells (×10³) | 0.49 ± 0.08 | 1.65 ± 0.18* | 6.21 ± 0.76* | 0.65 ± 0.17 | 0.84 ± 0.30 |
| CD62L$^{lo}$ CD44$^{high}$ CD8 T cells (×10³) | 0.11 ± 0.01 | 0.64 ± 0.11* | 1.96 ± 0.29* | 0.23 ± 0.10 | 0.27 ± 0.14 |

TABLE 1-continued

| | Absolute cell number after IL-7-Fc treatment | | | | |
|---|---|---|---|---|---|
| | Day 0 | Day 3 | Day 7 | Day 14 | Day 21 |
| γδ T cells (×10³) | 0.61 ± 0.14 | 2.40 ± 0.30* | 28.58 ± 3.88* | 2.05 ± 0.56* | 1.80 ± 0.07* |
| Conventional DC (×10³) | 0.33 ± 0.07 | 0.48 ± 0.09 | 2.15 ± 0.31* | 1.02 ± 0.12* | 0.56 ± 0.04 |
| Monocyte derived DC (×10³) | 4.78 ± 0.28 | 10.15 ± 0.83* | 38.89 ± 2.10* | 14.66 ± 2.16* | 5.64 ± 1.03 |

TABLE 2

| | 1 | 2 | 3 | 4 | 5 | Average ± STD |
|---|---|---|---|---|---|---|
| | % CD8 T cell in cervix/vagina | | | | | |
| PBS | 0.01 | 0.00 | 0.03 | 0.00 | 0.00 | 0.01 ± 0.01 |
| IL-7-Fc | 0.02 | 0.03 | 0.02 | 0.02 | 0.03 | 0.03 ± 0.01 |
| IFNα2a-Fc | 0.00 | 0.00 | 0.00 | 0.00 | 0.01 | 0.00 ± 0.00 |
| | % CD4 T cell in cervix/vagina | | | | | |
| PBS | 0.03 | 0.01 | 0.10 | 0.00 | 0.00 | 0.03 ± 0.04 |
| IL-7-Fc | 0.17 | 0.17 | 0.13 | 0.19 | 0.19 | 0.17 ± 0.03 |
| IFNα2a-Fc | 0.01 | 0.00 | 0.00 | 0.01 | 0.01 | 0.01 ± 0.00 |

Figure 4:
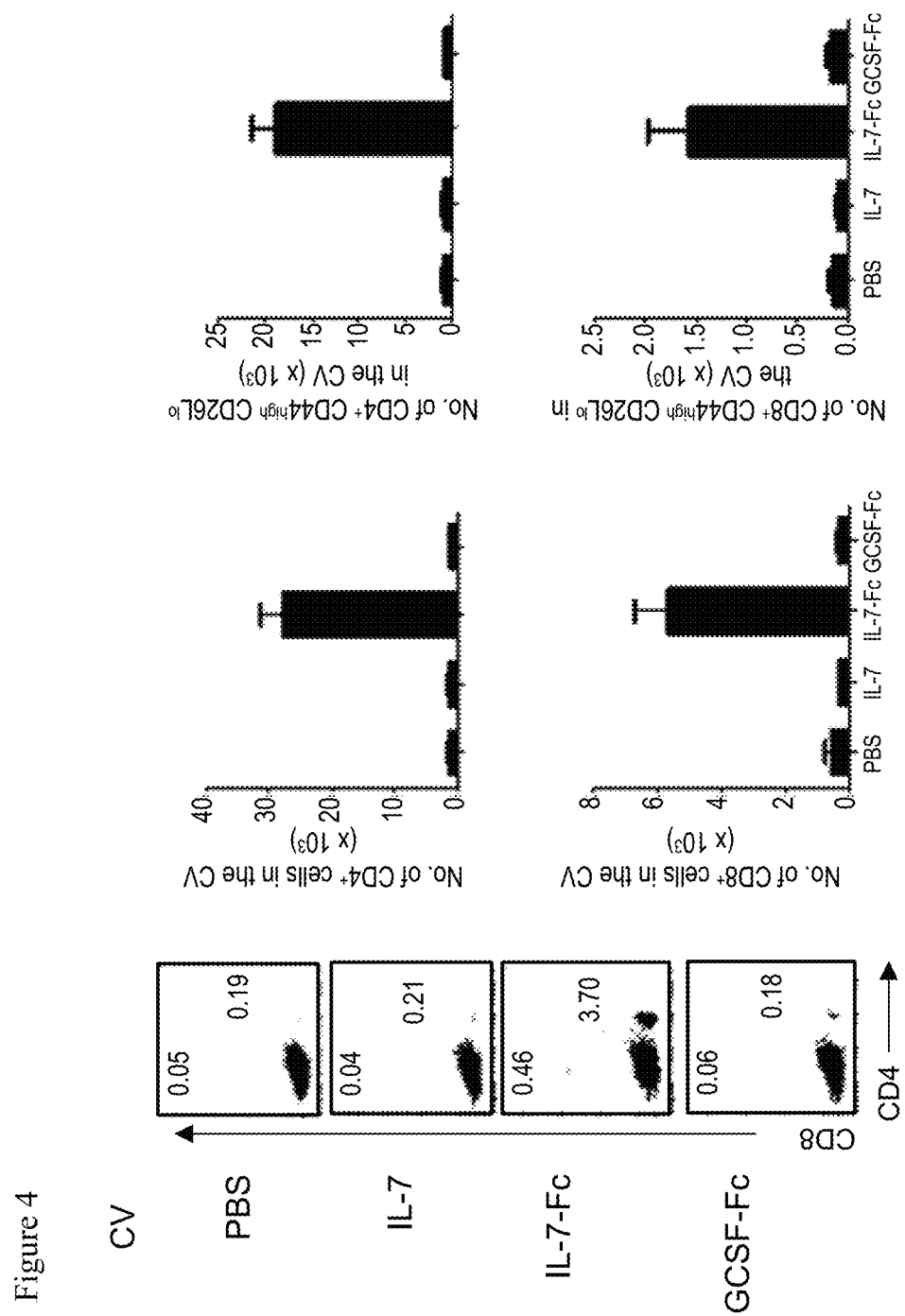
FIG. 4 shows the dot plot of the T cells, the number of CD4 and CD8 T cell counts, and the number of $CD62L^{low}CD44^{high}$ subsets in the CD4 and CD8 T cells (**, $p<0.01$), in cervical tissues.

As shown in Table 1 and FIG. 4, topical administration of IL-7-Fc increased the number of CD4 and CD8 T cells. This increase of genital tract T cells peaked at 7 days after IL-7-Fc administration and gradually decreased to the baseline levels at day 14. Moreover, the number of CD4 or CD8 T cells was significantly increased by about 20-fold and 10-fold, respectively, at 7 days after IL-7-Fc administration compared with the baseline levels. Particularly, the numbers of $CD44^{high}CD62L^{low}$ effector CD4 and CD8 T cells were significantly increased at day 7 and the number of total CD4 and CD8 T cells was decreased in a similar pattern over time.

As shown in Table 2 and FIG. 4, IFN-α2a-Fc, and G-CSF-Fc administration did not significantly change the number of CD4 and CD8 T cells compared to the baseline level or to the control group.

These results indicate that IL-7-Fc intravaginal administration induces local accumulation of immune cells such as T cells and DCs. Also, it was found that the effect of the IL-7-Fc intravaginal administration was superior to other immune inducers.

Example 4: Evaluation of Toxicity of IL-7-Fc

IL-7-Fc was intravaginally administered to SD rats five times, i.e., at day 1, 8, 15, 22, and 29. Sections of the genital tract were microscopically examined at 33 days post-initial treatment (Table 3A). Vaginal inflammation scores were recorded prior to administration and at 4 and 24 hours after administration using the scoring scale (Table 3B). The results are shown in Tables 3A and 3B.

TABLE 3A

| | | | Dose (mg/kg) | | | |
|---|---|---|---|---|---|---|
| Tissue | Observation | Severity | 0 | 0.8 | 3 | 8 |
| Total | | | 10 | 10 | 10 | 10 |
| Ovaries | Mineralization[a] | Minimal[c] | 1 | 0 | 2 | 0 |
| | | Within normal limit[e] | 9 | 10 | 8 | 10 |
| Uterus and | Infiltration[b] | Minimal[c] | 3 | 4 | 4 | 3 |
| | | Mild[d] | 0 | 0 | 0 | 2 |
| Cervix | | Within normal limit[e] | 7 | 6 | 6 | 5 |
| Vagina | Infiltration[b] | Minimal[c] | 4 | 3 | 3 | 6 |
| | | Mild[d] | 0 | 0 | 0 | 1 |
| | | Within normal limit[e] | 6 | 7 | 7 | 3 |

[a]Mineralization: the formation or deposition of minerals in a tissue
[b]Infiltration: the presence of mixed leukocyte (i.e. lymphocytes, dendritic cells, macrophage)
[c]Minimal: the amount of change barely exceeds normal limits
[d]Mild: easy identification of the lesion with limited severity and no functional impairment
[e]Within normal limits: the condition to be considered normal

TABLE 3B

| Dose | | Study interval (Day) | | | | | | | | | | | | | |
|---|---|---|---|---|---|---|---|---|---|---|---|---|---|---|---|
| (mg/kg) | Severity | 1[a] | 1[b] | 2[c] | 8[a] | 8[b] | 9[c] | 15[a] | 15[b] | 16[c] | 22[a] | 22[b] | 23[c] | 29[a] | 29[b] | 30[c] |
| 0 (n[d] = 15) | 0[e] | 15 | 15 | 15 | 15 | 15 | 15 | 15 | 15 | 15 | 15 | 15 | 15 | 14 | 14 | 15 |
| | 1[e] | 0 | 0 | 0 | 0 | 0 | 0 | 0 | 0 | 0 | 0 | 0 | 0 | 1 | 1 | 0 |
| | Total | 15 | 15 | 15 | 15 | 15 | 15 | 15 | 15 | 15 | 15 | 15 | 15 | 15 | 15 | 15 |
| 0.8 (n[d] = 10) | 0[e] | 10 | 10 | 10 | 10 | 10 | 10 | 10 | 10 | 10 | 10 | 10 | 10 | 10 | 10 | 10 |
| | Total | 10 | 10 | 10 | 10 | 10 | 10 | 10 | 10 | 10 | 10 | 10 | 10 | 10 | 10 | 10 |
| 3 (n[d] = 10) | 0[e] | 10 | 10 | 10 | 10 | 10 | 10 | 10 | 10 | 10 | 10 | 10 | 10 | 10 | 10 | 10 |
| | Total | 10 | 10 | 10 | 10 | 10 | 10 | 10 | 10 | 10 | 10 | 10 | 10 | 10 | 10 | 10 |
| 8 (n[d] = 15) | 0[e] | 15 | 15 | 15 | 15 | 15 | 15 | 15 | 15 | 14 | 15 | 15 | 15 | 15 | 15 | 15 |
| | 1[e] | 0 | 0 | 0 | 0 | 0 | 0 | 0 | 0 | 1 | 0 | 0 | 0 | 0 | 0 | 0 |
| | Total | 15 | 15 | 15 | 15 | 15 | 15 | 15 | 15 | 15 | 15 | 15 | 15 | 15 | 15 | 15 |

[a]predose
[b]4 hour postdose
[c]24 hour postdose
[d]Number of mice
[e]Vaginal irritation severity scoring scale: 0 = no erythema, 1 = very slight erythema (barely perceptible), 2 = well-defined erythema, 3 = moderate erythema, 4 = sever erythema (redness) to eschar formation As shown in Tables 3A and 3B above, pathological evaluation of the degree of inflammation of cervical tissues (Table 3A) and vagina (Table 3B) showed that the local administration of IL-7-Fc was safe and did not induce serious inflammation within genital tract.

Example 5: Confirmation of the Relationship Between the Administration Route of IL-7-Fc and the Induction of T Cells in the Cervix/Vaginal Tissues IL-7-Fc was administered subcutaneously or intravaginally to mice (n=5/group) and the distribution of T cells in the cervix/vaginal tissues was observed by the method of Preparation Example 6.

Figure 5:
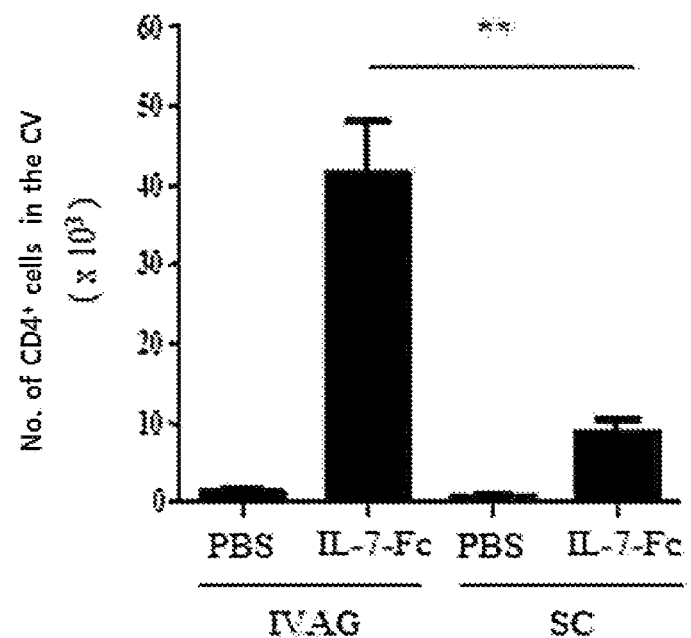
FIG. 5 shows the results of T cell mobilization depending on IL-7-Fc administration route. At 7 days after vaginal administration, T cells in cervical (CV) tissues were analyzed by flow cytometry, and the numbers of CD4 T cells and CD8 T cells were counted (FIG. 5) (**, $p<0.01$).
Figure 5:
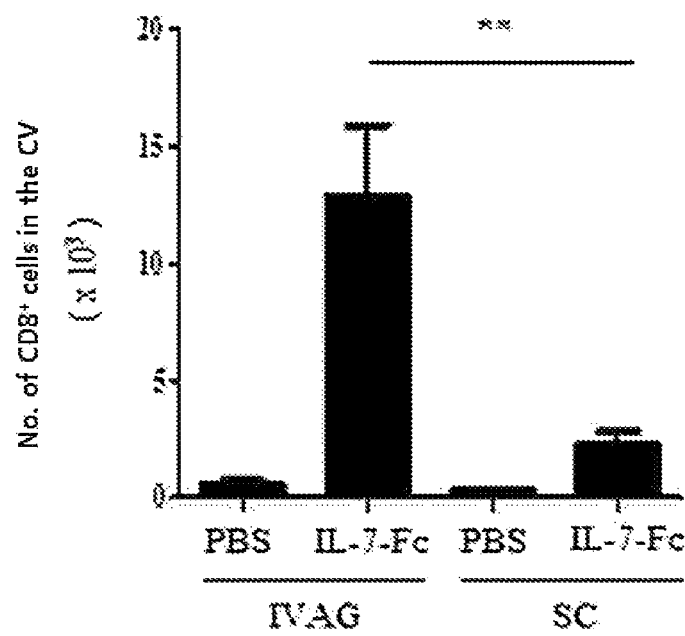

As a result, as shown in FIG. 5, the degree of accumulation of CD4 and CD8 T cells in the cervix/vaginal tissues was more increased by intravaginal administration than subcutaneous administration. Therefore, it was found that in order to induce CD4 and CD8 T cells specifically to the cervix/vaginal tissues, intravaginal administration which is directly related to the cervix/vaginal tissues is more effective than systemic administration such as subcutaneous administration.

Example 6: Anticancer Efficacy by Local Administration of IL-7-Fc Using TC-1/fluc Model The therapeutic efficacy was confirmed using a TC-1 tumor cell line expressing HPV16 E6 and HPV E7 antigens. $1 \times 10^6$ TC-1/fluc cell line (which was manipulated to express the luciferase gene in the TC-1 cell line expressing the HPV16 E6 and E7 gene) was administered intravaginally to the mice (n=7 or 8/group). Four (4) days before administration of the TC-1/fluc cell line, 3 mg of medroxyprogesterone acetate (Depo-Provera, Pfizer) was administered subcutaneously to the mice in the diestrus state. On the day of TC-1/fluc cell line administration, the mice were anesthetized and a mixture of 10 μl of 20% nonoxynol-9 (USP) and 40 μl of 3% carboxymethyl cellulose (CMC) (Sigma-Aldrich) was administered intravaginally to the mice, and 6 hours later, the mice were anesthetized again and their vaginas were washed with PBS and then TC-1/fluc cell line was administered to the mice.

Figure 6:
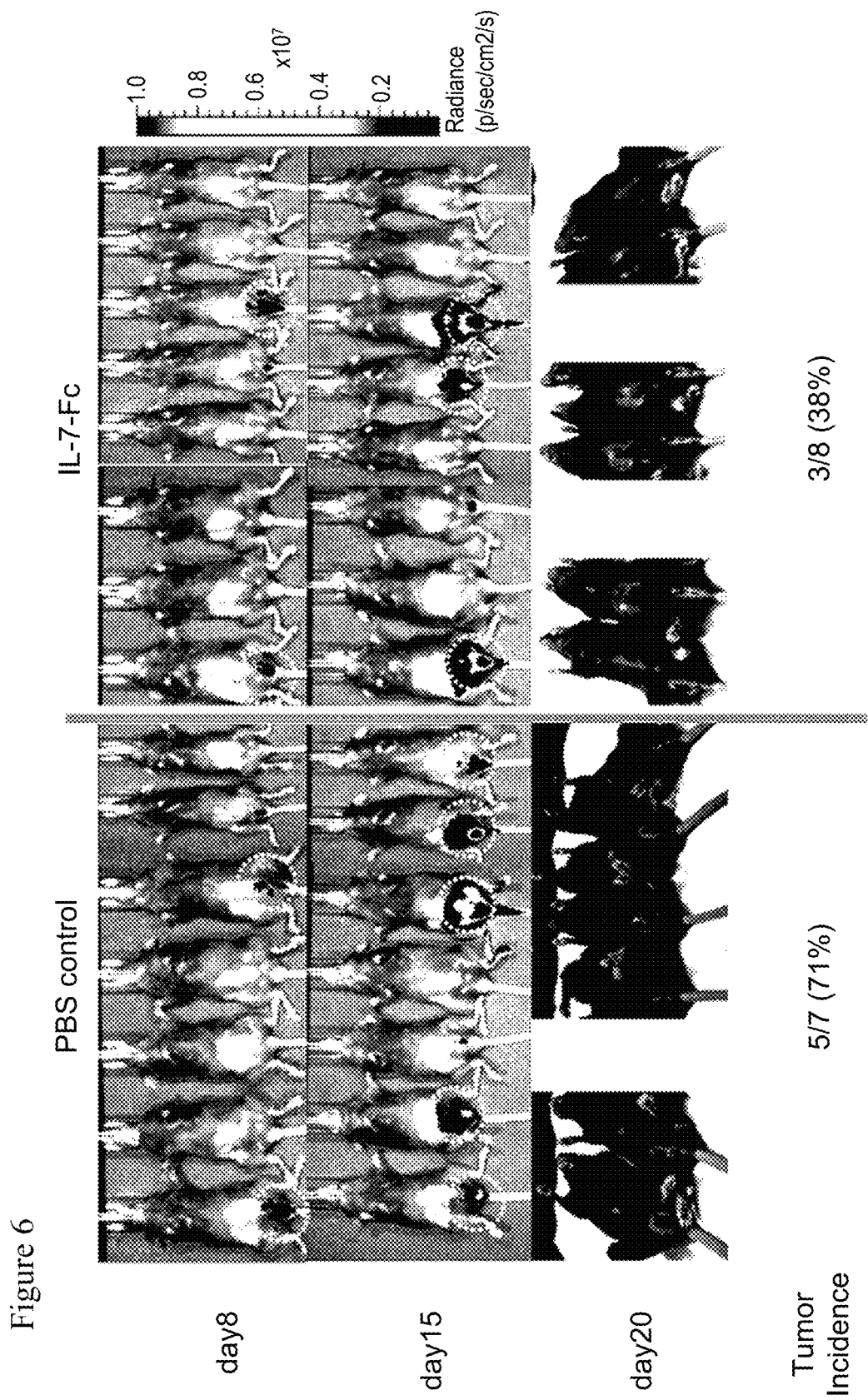
FIG. 6 shows the results of observing the anticancer effect depending on the administration of IL-7-Fc.

At 1, 8, and 15 days after TC-1/fluc cell line administration, 1 μg of IL-7-Fc was intravaginally administered to the mice, and the cancer progression was investigated by in vivo Bioluminescence imaging at days 8 and 15. At day 20, the anticancer effect was examined by observing the appearance (FIG. 6). As a result, it was confirmed that the incidence of cancer cells significantly decreased in the IL-7-Fc-treated group.

The invention claimed is:

1. A method for treating a genital disease in a subject in need thereof, comprising administering to the subject an effective amount of an interleukin-7 (IL-7) fusion protein,
wherein the genital disease is a human papillomavirus infection or cervical cancer,
wherein the administration is a local administration,
wherein the IL-7 fusion protein comprises a modified IL-7 and an immunoglobulin Fc region,
wherein the modified IL-7 has the following structure:
A-IL-7,
wherein
the A is an oligopeptide consisting of 1 to 10 amino acid residues selected from the group consisting of glycine and methionine, with proviso that when A is an oligopeptide of 1 amino acid residue, A is glycine; and
the IL-7 of the structure A-IL-7 is (i) an IL-7 comprising an amino acid sequence selected from the group consisting of SEQ ID NO: 1-6 or (ii) a peptide having an amino sequence which has a sequence identity of 95% or greater to the sequence set forth in SEQ ID NO: 1, and
wherein the immunoglobulin Fc region has the following Formula (I)

N'-(Z1)p-(Y)q-Z2-Z3-Z4-C'     Formula (I)

wherein
N' is the N-terminus of a polypeptide and C' is the C-terminus of the polypeptide,
p or q is an integer of 0 or 1,
Z1 is an amino acid sequence comprising 5 to 9 consecutive amino acid residues in the N-terminus direction starting from the 98th position of SEQ ID NO: 7,
Y is an amino acid sequence comprising 5 to 64 consecutive amino acid residues in the N-terminus direction starting from the 162nd position of SEQ ID NO: 7,
Z2 is an amino acid sequence comprising 4 to 37 consecutive amino acid residues in the C-terminus direction starting from the 163rd position of SEQ ID NO: 7,
Z3 is an amino acid sequence comprising 70 to 106 consecutive amino acid residues in the N-terminus direction starting from the 220th position of SEQ ID NO: 8, and
Z4 is an amino acid sequence comprising 80 to 107 consecutive amino acid residues in the C-terminus direction starting from the 221st position of SEQ ID NO: 8.

2. The method of claim 1, wherein the local administration is a mucosal administration.

3. The method of claim 1, wherein the IL-7 is fused to the N-terminus or C-terminus of the immunoglobulin Fc region.

4. The method of claim 1, wherein the IL-7 comprises an amino acid sequence selected from the group consisting of SEQ ID NOS: 1 to 6.

5. The method of claim 1, wherein the A is selected from the group consisting of glycine, methionine-methionine, glycine-glycine, methionine-glycine, glycine-methionine, methionine-methionine-methionine, methionine-methionine-glycine, methionine-glycine-methionine, glycine-methionine-methionine, methionine-glycine-glycine, glycine-methionine-glycine, glycine-glycine-methionine, methionine-methionine-methionine, and glycine-glycine-glycine.

6. The method of claim 1, wherein the modified immunoglobulin Fc region is selected from the group consisting of SEQ ID NO: 9 to 14.

7. The method of claim 1, wherein the oligopeptide A consists of 1 to 5 amino acid residues selected from the group consisting of glycine and methionine.

8. The method of claim 1, wherein the IL-7 is fused to the N-terminus of the immunoglobulin Fc region.

9. A method for treating a human papillomavirus infection or cervical cancer in a subject in need thereof, comprising administering to the subject an effective amount of an interleukin-7 (IL-7) fusion protein via a mucosal administration,
wherein the IL-7 fusion protein comprises an IL-7 and an immunoglobulin Fc region,
wherein the IL-7 is any one of the following (i)-(iii):
(i) an IL-7 comprising an amino acid sequence selected from the group consisting of SEQ ID NO: 1-6;
(ii) a peptide having an amino sequence which has a sequence identity of 95% or greater to the sequence set forth in SEQ ID NO: 1; and
(iii) a modified IL-7 having the following structure:
A-IL-7,
wherein
the A is an oligopeptide consisting of 1 to 10 amino acid residues selected from the group consisting of glycine and methionine, with proviso that when A is an oligopeptide of 1 amino acid residue, A is glycine; and
the IL-7 is the IL-7 of (i) or the peptide of (ii), and
wherein the immunoglobulin Fc region has the following formula (I)

N'-(Z1)p-(Y)q-Z2-Z3-Z4-C'     Formula (I)

wherein
N' is the N-terminus of a polypeptide and C' is the C-terminus of the polypeptide,
p or q is an integer of 0 or 1,
Z1 is an amino acid sequence comprising 5 to 9 consecutive amino acid residues in the N-terminus direction starting from the 98th position of SEQ ID NO: 7,
Y is an amino acid sequence comprising 5 to 64 consecutive amino acid residues in the N-terminus direction starting from the 162nd position of SEQ ID NO: 7,
Z2 is an amino acid sequence comprising 4 to 37 consecutive amino acid residues in the C-terminus direction starting from the 163rd position of SEQ ID NO: 7,
Z3 is an amino acid sequence comprising 70 to 106 consecutive amino acid residues in the N-terminus direction starting from the 220th position of SEQ ID NO: 8, and
Z4 is an amino acid sequence comprising 80 to 107 consecutive amino acid residues in the C-terminus direction starting from the 221st position of SEQ ID NO: 8.

10. The method of claim 9, wherein the IL-7 is fused to the N-terminus or C-terminus of the immunoglobulin Fc region.

11. The method of claim 9, wherein the IL-7 is the (iii) modified IL-7.

12. The method of claim 9, wherein the IL-7 comprises an amino acid sequence selected from the group consisting of SEQ ID NOS: 1 to 6.

13. The method of claim 9, wherein the A is selected from the group consisting of glycine, methionine-methionine, glycine-glycine, methionine-glycine, glycine-methionine, methionine-methionine-methionine, methionine-methionine-glycine, methionine-glycine-methionine, glycine-methionine-methionine, methionine-glycine-glycine, glycine-methionine-glycine, glycine-glycine-methionine, methionine-methionine-methionine, and glycine-glycine-glycine.

14. The method of claim 9, wherein the modified immunoglobulin Fc region is selected from the group consisting of SEQ ID NO: 9 to 14.

15. The method of claim 9, wherein the oligopeptide A consists of 1 to 5 amino acid residues selected from the group consisting of glycine and methionine.

16. The method of claim 9, wherein the IL-7 is fused to the N-terminus of the immunoglobulin Fc region.

* * * * *

SEQUENCE LISTING

```
<160> NUMBER OF SEQ ID NOS: 40

<210> SEQ ID NO 1
<211> LENGTH: 177
<212> TYPE: PRT
<213> ORGANISM: Artificial Sequence
<220> FEATURE:
<223> OTHER INFORMATION: amino acid sequence of human IL-7 (Accession
      number : P13232)

<400> SEQUENCE: 1

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175
```

His

<210> SEQ ID NO 2
<211> LENGTH: 154
<212> TYPE: PRT
<213> ORGANISM: Artificial Sequence
<220> FEATURE:
<223> OTHER INFORMATION: amino acid sequence of rat IL-7 (Accession number : P56478)

<400> SEQUENCE: 2

```
Met Phe His Val Ser Phe Arg Tyr Ile Phe Gly Ile Pro Pro Leu Ile
1               5                   10                  15

Leu Val Leu Leu Pro Val Thr Ser Ser Asp Cys His Ile Lys Asp Lys
            20                  25                  30

Asp Gly Lys Ala Phe Gly Ser Val Leu Met Ile Ser Ile Asn Gln Leu
        35                  40                  45

Asp Lys Met Thr Gly Thr Asp Ser Asp Cys Pro Asn Asn Glu Pro Asn
50                  55                  60

Phe Phe Lys Lys His Leu Cys Asp Asp Thr Lys Glu Ala Ala Phe Leu
65                  70                  75                  80

Asn Arg Ala Ala Arg Lys Leu Arg Gln Phe Leu Lys Met Asn Ile Ser
                85                  90                  95

Glu Glu Phe Asn Asp His Leu Leu Arg Val Ser Asp Gly Thr Gln Thr
            100                 105                 110

Leu Val Asn Cys Thr Ser Lys Glu Glu Lys Thr Ile Lys Glu Gln Lys
        115                 120                 125

Lys Asn Asp Pro Cys Phe Leu Lys Arg Leu Leu Arg Glu Ile Lys Thr
130                 135                 140

Cys Trp Asn Lys Ile Leu Lys Gly Ser Ile
145                 150
```

<210> SEQ ID NO 3
<211> LENGTH: 154
<212> TYPE: PRT
<213> ORGANISM: Artificial Sequence
<220> FEATURE:
<223> OTHER INFORMATION: amino acid sequence of mouse IL-7 (Accession number : P10168)

<400> SEQUENCE: 3

```
Met Phe His Val Ser Phe Arg Tyr Ile Phe Gly Ile Pro Pro Leu Ile
1               5                   10                  15

Leu Val Leu Leu Pro Val Thr Ser Ser Glu Cys His Ile Lys Asp Lys
            20                  25                  30

Glu Gly Lys Ala Tyr Glu Ser Val Leu Met Ile Ser Ile Asp Glu Leu
        35                  40                  45

Asp Lys Met Thr Gly Thr Asp Ser Asn Cys Pro Asn Asn Glu Pro Asn
50                  55                  60

Phe Phe Arg Lys His Val Cys Asp Asp Thr Lys Glu Ala Ala Phe Leu
65                  70                  75                  80

Asn Arg Ala Ala Arg Lys Leu Lys Gln Phe Leu Lys Met Asn Ile Ser
                85                  90                  95

Glu Glu Phe Asn Val His Leu Leu Thr Val Ser Gln Gly Thr Gln Thr
            100                 105                 110

Leu Val Asn Cys Thr Ser Lys Glu Glu Lys Asn Val Lys Glu Gln Lys
        115                 120                 125
```

```
Lys Asn Asp Ala Cys Phe Leu Lys Arg Leu Leu Arg Glu Ile Lys Thr
        130                 135                 140

Cys Trp Asn Lys Ile Leu Lys Gly Ser Ile
145                 150

<210> SEQ ID NO 4
<211> LENGTH: 177
<212> TYPE: PRT
<213> ORGANISM: Artificial Sequence
<220> FEATURE:
<223> OTHER INFORMATION: amino acid sequence of monkey IL-7 (Accession
      number : NP_001279008)

<400> SEQUENCE: 4

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Leu Cys Asp Asp Asn Lys Glu Gly Met Phe
65                  70                  75                  80

Leu Phe Arg Ala Ala Arg Lys Leu Lys Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Lys Val Lys Gly Arg Lys Pro Ala Ala
        115                 120                 125

Leu Gly Glu Pro Gln Pro Thr Lys Ser Leu Glu Glu Asn Lys Ser Leu
    130                 135                 140

Lys Glu Gln Lys Lys Leu Asn Asp Ser Cys Phe Leu Lys Arg Leu Leu
145                 150                 155                 160

Gln Lys Ile Lys Thr Cys Trp Asn Lys Ile Leu Met Gly Thr Lys Glu
                165                 170                 175

His

<210> SEQ ID NO 5
<211> LENGTH: 176
<212> TYPE: PRT
<213> ORGANISM: Artificial Sequence
<220> FEATURE:
<223> OTHER INFORMATION: amino acid sequence of cow IL-7 (Accession
      number : P26895)

<400> SEQUENCE: 5

Met Phe His Val Ser Phe Arg Tyr Ile Phe Gly Ile Pro Pro Leu Ile
1               5                   10                  15

Leu Val Leu Leu Pro Val Ala Ser Ser Asp Cys Asp Ile Ser Gly Lys
            20                  25                  30

Asp Gly Gly Ala Tyr Gln Asn Val Leu Met Val Asn Ile Asp Asp Leu
        35                  40                  45

Asp Asn Met Ile Asn Phe Asp Ser Asn Cys Leu Asn Asn Glu Pro Asn
    50                  55                  60

Phe Phe Lys Lys His Ser Cys Asp Asp Asn Lys Glu Ala Ser Phe Leu
65                  70                  75                  80

Asn Arg Ala Ser Arg Lys Leu Arg Gln Phe Leu Lys Met Asn Ile Ser
```

```
                    85                  90                  95
Asp Asp Phe Lys Leu His Leu Ser Thr Val Ser Gln Gly Thr Leu Thr
                100                 105                 110

Leu Leu Asn Cys Thr Ser Lys Gly Lys Gly Arg Lys Pro Pro Ser Leu
            115                 120                 125

Ser Glu Ala Gln Pro Thr Lys Asn Leu Glu Glu Asn Lys Ser Ser Lys
        130                 135                 140

Glu Gln Lys Lys Gln Asn Asp Leu Cys Phe Leu Lys Ile Leu Leu Gln
145                 150                 155                 160

Lys Ile Lys Thr Cys Trp Asn Lys Ile Leu Arg Gly Ile Lys Glu His
                165                 170                 175

<210> SEQ ID NO 6
<211> LENGTH: 176
<212> TYPE: PRT
<213> ORGANISM: Artificial Sequence
<220> FEATURE:
<223> OTHER INFORMATION: amino acid sequence of sheep IL-7 (Accession
      number : Q28540)

<400> SEQUENCE: 6

Met Phe His Val Ser Phe Arg Tyr Ile Phe Gly Ile Pro Pro Leu Ile
1               5                   10                  15

Leu Val Leu Leu Pro Val Ala Ser Ser Asp Cys Asp Phe Ser Gly Lys
                20                  25                  30

Asp Gly Gly Ala Tyr Gln Asn Val Leu Met Val Ser Ile Asp Asp Leu
            35                  40                  45

Asp Asn Met Ile Asn Phe Asp Ser Asn Cys Leu Asn Asn Glu Pro Asn
        50                  55                  60

Phe Phe Lys Lys His Ser Cys Asp Asp Asn Lys Glu Ala Ser Phe Leu
65                  70                  75                  80

Asn Arg Ala Ala Arg Lys Leu Lys Gln Phe Leu Lys Met Asn Ile Ser
                85                  90                  95

Asp Asp Phe Lys Leu His Leu Ser Thr Val Ser Gln Gly Thr Leu Thr
                100                 105                 110

Leu Leu Asn Cys Thr Ser Lys Gly Lys Gly Arg Lys Pro Pro Ser Leu
            115                 120                 125

Gly Glu Ala Gln Pro Thr Lys Asn Leu Glu Glu Asn Lys Ser Leu Lys
        130                 135                 140

Glu Gln Arg Lys Gln Asn Asp Leu Cys Phe Leu Lys Ile Leu Leu Gln
145                 150                 155                 160

Lys Ile Lys Thr Cys Trp Asn Lys Ile Leu Arg Gly Ile Thr Glu His
                165                 170                 175

<210> SEQ ID NO 7
<211> LENGTH: 384
<212> TYPE: PRT
<213> ORGANISM: Artificial Sequence
<220> FEATURE:
<223> OTHER INFORMATION: amino acid sequence of human IgD constant
      region (Genbank accession No. P01880)

<400> SEQUENCE: 7

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
                20                  25                  30

Tyr His Pro Thr Ser Val Thr Val Thr Trp Tyr Met Gly Thr Gln Ser
```

```
              35                  40                  45
Gln Pro Gln Arg Thr Phe Pro Glu Ile Gln Arg Arg Asp Ser Tyr Tyr
 50                  55                  60

Met Thr Ser Ser Gln Leu Ser Thr Pro Leu Gln Gln Trp Arg Gln Gly
 65                  70                  75                  80

Glu Tyr Lys Cys Val Gln His Thr Ala Ser Lys Ser Lys Lys Glu
                 85                  90                  95

Ile Phe Arg Trp Pro Glu Ser Pro Lys Ala Gln Ala Ser Ser Val Pro
                100                 105                 110

Thr Ala Gln Pro Gln Ala Glu Gly Ser Leu Ala Lys Ala Thr Thr Ala
                115                 120                 125

Pro Ala Thr Thr Arg Asn Thr Gly Arg Gly Gly Glu Glu Lys Lys Lys
                130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
                180                 185                 190

Val Gly Ser Asp Leu Lys Asp Ala His Leu Thr Trp Glu Val Ala Gly
                195                 200                 205

Lys Val Pro Thr Gly Gly Val Glu Glu Gly Leu Leu Glu Arg His Ser
                210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
                260                 265                 270

Val Lys Leu Ser Leu Asn Leu Leu Ala Ser Ser Asp Pro Pro Glu Ala
                275                 280                 285

Ala Ser Trp Leu Leu Cys Glu Val Ser Gly Phe Ser Pro Pro Asn Ile
                290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
                325                 330                 335

Trp Ser Val Leu Arg Val Pro Ala Pro Pro Ser Pro Gln Pro Ala Thr
                340                 345                 350

Tyr Thr Cys Val Val Ser His Glu Asp Ser Arg Thr Leu Leu Asn Ala
                355                 360                 365

Ser Arg Ser Leu Glu Val Ser Tyr Val Thr Asp His Gly Pro Met Lys
370                 375                 380

<210> SEQ ID NO 8
<211> LENGTH: 327
<212> TYPE: PRT
<213> ORGANISM: Artificial Sequence
<220> FEATURE:
<223> OTHER INFORMATION: amino acid sequence of Partial human IgG4
      constant region (Genbank accession No. AAH25985)

<400> SEQUENCE: 8

Ala Ser Thr Lys Gly Pro Ser Val Phe Pro Leu Ala Pro Cys Ser Arg
 1                   5                  10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 9
<211> LENGTH: 245
<212> TYPE: PRT
<213> ORGANISM: Artificial Sequence
<220> FEATURE:
<223> OTHER INFORMATION: amino acid sequence of hFc01

<400> SEQUENCE: 9

Arg Asn Thr Gly Arg Gly Gly Glu Glu Lys Lys Lys Glu Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
        35                  40                  45
```

-continued

Leu Met Ile Ser Arg Thr Pro Glu Val Thr Cys Val Val Asp Val
 50                  55                  60

Ser Gln Glu Asp Pro Glu Val Gln Phe Asn Trp Tyr Val Asp Gly Val
 65                  70                  75                  80

Glu Val His Asn Ala Lys Thr Lys Pro Arg Glu Glu Gln Phe Asn Ser
                 85                  90                  95

Thr Tyr Arg Val Val Ser Val Leu Thr Val Leu His Gln Asp Trp Leu
                100                 105                 110

Asn Gly Lys Glu Tyr Lys Cys Lys Val Ser Asn Lys Gly Leu Pro Ser
                115                 120                 125

Ser Ile Glu Lys Thr Ile Ser Lys Ala Lys Gly Gln Pro Arg Glu Pro
130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
                180                 185                 190

Pro Pro Val Leu Asp Ser Asp Gly Ser Phe Phe Leu Tyr Ser Arg Leu
                195                 200                 205

Thr Val Asp Lys Ser Arg Trp Gln Glu Gly Asn Val Phe Ser Cys Ser
210                 215                 220

Val Met His Glu Ala Leu His Asn His Tyr Thr Gln Lys Ser Leu Ser
225                 230                 235                 240

Leu Ser Leu Gly Lys
                245

<210> SEQ ID NO 10
<211> LENGTH: 245
<212> TYPE: PRT
<213> ORGANISM: Artificial Sequence
<220> FEATURE:
<223> OTHER INFORMATION: amino acid sequence of hFc02

<400> SEQUENCE: 10

Arg Asn Thr Gly Arg Gly Gly Glu Glu Lys Lys Gly Gly Lys Glu Lys
1               5                   10                  15

Glu Glu Gln Glu Glu Arg Glu Thr Lys Thr Pro Glu Cys Pro Ser His
                20                  25                  30

Thr Gln Pro Leu Gly Val Phe Leu Phe Pro Pro Lys Pro Lys Asp Thr
            35                  40                  45

Leu Met Ile Ser Arg Thr Pro Glu Val Thr Cys Val Val Asp Val
 50                  55                  60

Ser Gln Glu Asp Pro Glu Val Gln Phe Asn Trp Tyr Val Asp Gly Val
 65                  70                  75                  80

Glu Val His Asn Ala Lys Thr Lys Pro Arg Glu Glu Gln Phe Asn Ser
                 85                  90                  95

Thr Tyr Arg Val Val Ser Val Leu Thr Val Leu His Gln Asp Trp Leu
                100                 105                 110

Asn Gly Lys Glu Tyr Lys Cys Lys Val Ser Asn Lys Gly Leu Pro Ser
                115                 120                 125

Ser Ile Glu Lys Thr Ile Ser Lys Ala Lys Gly Gln Pro Arg Glu Pro
130                 135                 140

Gln Val Tyr Thr Leu Pro Pro Ser Gln Glu Glu Met Thr Lys Asn Gln
145                 150                 155                 160

```
Val Ser Leu Thr Cys Leu Val Lys Gly Phe Tyr Pro Ser Asp Ile Ala
            165                 170                 175

Val Glu Trp Glu Ser Asn Gly Gln Pro Glu Asn Asn Tyr Lys Thr Thr
        180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
        210                 215                 220

Val Met His Glu Ala Leu His Asn His Tyr Thr Gln Lys Ser Leu Ser
225                 230                 235                 240

Leu Ser Leu Gly Lys
                245

<210> SEQ ID NO 11
<211> LENGTH: 245
<212> TYPE: PRT
<213> ORGANISM: Artificial Sequence
<220> FEATURE:
<223> OTHER INFORMATION: amino acid sequence of hFc03

<400> SEQUENCE: 11

Arg Asn Thr Gly Arg Gly Gly Glu Glu Lys Lys Gly Ser Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
            165                 170                 175

Val Glu Trp Glu Ser Asn Gly Gln Pro Glu Asn Asn Tyr Lys Thr Thr
        180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
        210                 215                 220

Val Met His Glu Ala Leu His Asn His Tyr Thr Gln Lys Ser Leu Ser
225                 230                 235                 240

Leu Ser Leu Gly Lys
                245

<210> SEQ ID NO 12
<211> LENGTH: 245
```

```
<212> TYPE: PRT
<213> ORGANISM: Artificial Sequence
<220> FEATURE:
<223> OTHER INFORMATION: amino acid sequence of hFc04

<400> SEQUENCE: 12
```

Arg Asn Thr Gly Arg Gly Gly Glu Glu Lys Lys Ser Gly Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Leu Gly Lys
                245

```
<210> SEQ ID NO 13
<211> LENGTH: 245
<212> TYPE: PRT
<213> ORGANISM: Artificial Sequence
<220> FEATURE:
<223> OTHER INFORMATION: amino acid sequence of hFc05

<400> SEQUENCE: 13
```

Arg Asn Thr Gly Arg Gly Gly Glu Glu Lys Lys Ser Ser Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

```
Glu Val His Asn Ala Lys Thr Lys Pro Arg Glu Glu Gln Phe Asn Ser
                 85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
            115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
            195                 200                 205

Thr Val Asp Lys Ser Arg Trp Gln Glu Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Leu Gly Lys
                245

<210> SEQ ID NO 14
<211> LENGTH: 243
<212> TYPE: PRT
<213> ORGANISM: Artificial Sequence
<220> FEATURE:
<223> OTHER INFORMATION: amino acid sequence of mouse IgG Fc variant

<400> SEQUENCE: 14

Ala Ser Ala Glu Pro Arg Gly Pro Thr Ile Lys Pro Cys Pro Pro Cys
1               5                   10                  15

Lys Cys Pro Ala Pro Asn Leu Glu Gly Gly Pro Ser Val Phe Ile Phe
            20                  25                  30

Pro Pro Lys Ile Lys Asp Val Leu Met Ile Ser Leu Ser Pro Ile Val
            35                  40                  45

Thr Cys Val Val Val Asp Val Ser Glu Asp Asp Pro Asp Val Gln Ile
    50                  55                  60

Ser Trp Phe Val Asn Asn Val Glu Val His Thr Ala Gln Thr Gln Thr
65                  70                  75                  80

His Arg Glu Asp Tyr Asn Ser Thr Leu Arg Val Val Ser Ala Leu Pro
                85                  90                  95

Ile Gln His Gln Asp Trp Met Ser Gly Lys Ala Phe Ala Cys Ala Val
            100                 105                 110

Asn Asn Lys Asp Leu Pro Ala Pro Ile Glu Arg Thr Ile Ser Lys Pro
            115                 120                 125

Lys Gly Ser Val Arg Ala Pro Gln Val Tyr Val Leu Pro Pro Pro Glu
    130                 135                 140

Glu Glu Met Thr Lys Lys Gln Val Thr Leu Thr Cys Met Val Thr Asp
145                 150                 155                 160

Phe Met Pro Glu Asp Ile Tyr Val Glu Trp Thr Asn Asn Gly Lys Thr
                165                 170                 175

Glu Leu Asn Tyr Lys Asn Thr Glu Pro Val Leu Asp Ser Asp Gly Ser
            180                 185                 190
```

```
Tyr Phe Met Tyr Ser Lys Leu Arg Val Glu Lys Lys Asn Trp Val Glu
            195                 200                 205

Arg Asn Ser Tyr Ser Cys Ser Val Val His Glu Gly Leu His Asn His
210                 215                 220

His Thr Thr Lys Ser Phe Ser Arg Thr Pro Gly Lys Gly Gly Asn
225                 230                 235                 240

Ser Gly Ser

<210> SEQ ID NO 15
<211> LENGTH: 153
<212> TYPE: PRT
<213> ORGANISM: Artificial Sequence
<220> FEATURE:
<223> OTHER INFORMATION: amino acid sequence of modified IL-7(M)

<400> SEQUENCE: 15

Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30

Ser Asn Cys Leu Asn Asn Glu Phe Asn Phe Phe Lys Arg His Ile Cys
        35                  40                  45

Asp Ala Asn Lys Glu Gly Met Phe Leu Phe Arg Ala Ala Arg Lys Leu
    50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
        115                 120                 125

Leu Cys Phe Leu Lys Arg Leu Leu Gln Glu Ile Lys Thr Cys Trp Asn
    130                 135                 140

Lys Ile Leu Met Gly Thr Lys Glu His
145                 150

<210> SEQ ID NO 16
<211> LENGTH: 154
<212> TYPE: PRT
<213> ORGANISM: Artificial Sequence
<220> FEATURE:
<223> OTHER INFORMATION: amino acid sequence of modified IL-7(MM)

<400> SEQUENCE: 16

Met Met Asp Cys Asp Ile Glu Gly Lys Asp Gly Lys Gln Tyr Glu Ser
1               5                   10                  15

Val Leu Met Val Ser Ile Asp Gln Leu Leu Asp Ser Met Lys Glu Ile
            20                  25                  30

Gly Ser Asn Cys Leu Asn Asn Glu Phe Asn Phe Phe Lys Arg His Ile
        35                  40                  45

Cys Asp Ala Asn Lys Glu Gly Met Phe Leu Phe Arg Ala Ala Arg Lys
    50                  55                  60

Leu Arg Gln Phe Leu Lys Met Asn Ser Thr Gly Asp Phe Asp Leu His
65                  70                  75                  80

Leu Leu Lys Val Ser Glu Gly Thr Thr Ile Leu Leu Asn Cys Thr Gly
                85                  90                  95
```

Gln Val Lys Gly Arg Lys Pro Ala Ala Leu Gly Glu Ala Gln Pro Thr
            100                 105                 110
Lys Ser Leu Glu Glu Asn Lys Ser Leu Lys Glu Gln Lys Lys Leu Asn
        115                 120                 125
Asp Leu Cys Phe Leu Lys Arg Leu Leu Gln Glu Ile Lys Thr Cys Trp
130                 135                 140
Asn Lys Ile Leu Met Gly Thr Lys Glu His
145                 150

<210> SEQ ID NO 17
<211> LENGTH: 155
<212> TYPE: PRT
<213> ORGANISM: Artificial Sequence
<220> FEATURE:
<223> OTHER INFORMATION: amino acid sequence of modified IL-7(MMM)

<400> SEQUENCE: 17

Met Met Met Asp Cys Asp Ile Glu Gly Lys Asp Gly Lys Gln Tyr Glu
1               5                   10                  15
Ser Val Leu Met Val Ser Ile Asp Gln Leu Leu Asp Ser Met Lys Glu
            20                  25                  30
Ile Gly Ser Asn Cys Leu Asn Asn Glu Phe Asn Phe Phe Lys Arg His
        35                  40                  45
Ile Cys Asp Ala Asn Lys Glu Gly Met Phe Leu Phe Arg Ala Ala Arg
    50                  55                  60
Lys Leu Arg Gln Phe Leu Lys Met Asn Ser Thr Gly Asp Phe Asp Leu
65                  70                  75                  80
His Leu Leu Lys Val Ser Glu Gly Thr Thr Ile Leu Leu Asn Cys Thr
                85                  90                  95
Gly Gln Val Lys Gly Arg Lys Pro Ala Ala Leu Gly Glu Ala Gln Pro
            100                 105                 110
Thr Lys Ser Leu Glu Glu Asn Lys Ser Leu Lys Glu Gln Lys Lys Leu
        115                 120                 125
Asn Asp Leu Cys Phe Leu Lys Arg Leu Leu Gln Glu Ile Lys Thr Cys
    130                 135                 140
Trp Asn Lys Ile Leu Met Gly Thr Lys Glu His
145                 150                 155

<210> SEQ ID NO 18
<211> LENGTH: 155
<212> TYPE: PRT
<213> ORGANISM: Artificial Sequence
<220> FEATURE:
<223> OTHER INFORMATION: amino acid sequence of modified IL-7(MGM)

<400> SEQUENCE: 18

Met Gly Met Asp Cys Asp Ile Glu Gly Lys Asp Gly Lys Gln Tyr Glu
1               5                   10                  15
Ser Val Leu Met Val Ser Ile Asp Gln Leu Leu Asp Ser Met Lys Glu
            20                  25                  30
Ile Gly Ser Asn Cys Leu Asn Asn Glu Phe Asn Phe Phe Lys Arg His
        35                  40                  45
Ile Cys Asp Ala Asn Lys Glu Gly Met Phe Leu Phe Arg Ala Ala Arg
    50                  55                  60
Lys Leu Arg Gln Phe Leu Lys Met Asn Ser Thr Gly Asp Phe Asp Leu
65                  70                  75                  80
His Leu Leu Lys Val Ser Glu Gly Thr Thr Ile Leu Leu Asn Cys Thr

```
            85                  90                  95

Gly Gln Val Lys Gly Arg Lys Pro Ala Ala Leu Gly Glu Ala Gln Pro
            100                 105                 110

Thr Lys Ser Leu Glu Glu Asn Lys Ser Leu Lys Glu Gln Lys Lys Leu
        115                 120                 125

Asn Asp Leu Cys Phe Leu Lys Arg Leu Leu Gln Glu Ile Lys Thr Cys
    130                 135                 140

Trp Asn Lys Ile Leu Met Gly Thr Lys Glu His
145                 150                 155

<210> SEQ ID NO 19
<211> LENGTH: 155
<212> TYPE: PRT
<213> ORGANISM: Artificial Sequence
<220> FEATURE:
<223> OTHER INFORMATION: amino acid sequence of modified IL-7(DDD)

<400> SEQUENCE: 19

Asp Asp Asp Asp Cys Asp Ile Glu Gly Lys Asp Gly Lys Gln Tyr Glu
1               5                   10                  15

Ser Val Leu Met Val Ser Ile Asp Gln Leu Leu Asp Ser Met Lys Glu
            20                  25                  30

Ile Gly Ser Asn Cys Leu Asn Asn Glu Phe Asn Phe Phe Lys Arg His
        35                  40                  45

Ile Cys Asp Ala Asn Lys Glu Gly Met Phe Leu Phe Arg Ala Ala Arg
    50                  55                  60

Lys Leu Arg Gln Phe Leu Lys Met Asn Ser Thr Gly Asp Phe Asp Leu
65                  70                  75                  80

His Leu Leu Lys Val Ser Glu Gly Thr Thr Ile Leu Leu Asn Cys Thr
            85                  90                  95

Gly Gln Val Lys Gly Arg Lys Pro Ala Ala Leu Gly Glu Ala Gln Pro
            100                 105                 110

Thr Lys Ser Leu Glu Glu Asn Lys Ser Leu Lys Glu Gln Lys Lys Leu
        115                 120                 125

Asn Asp Leu Cys Phe Leu Lys Arg Leu Leu Gln Glu Ile Lys Thr Cys
    130                 135                 140

Trp Asn Lys Ile Leu Met Gly Thr Lys Glu His
145                 150                 155

<210> SEQ ID NO 20
<211> LENGTH: 156
<212> TYPE: PRT
<213> ORGANISM: Artificial Sequence
<220> FEATURE:
<223> OTHER INFORMATION: amino acid sequence of modified IL-7(MMMM)

<400> SEQUENCE: 20

Met Met Met Met Asp Cys Asp Ile Glu Gly Lys Asp Gly Lys Gln Tyr
1               5                   10                  15

Glu Ser Val Leu Met Val Ser Ile Asp Gln Leu Leu Asp Ser Met Lys
            20                  25                  30

Glu Ile Gly Ser Asn Cys Leu Asn Asn Glu Phe Asn Phe Phe Lys Arg
        35                  40                  45

His Ile Cys Asp Ala Asn Lys Glu Gly Met Phe Leu Phe Arg Ala Ala
    50                  55                  60

Arg Lys Leu Arg Gln Phe Leu Lys Met Asn Ser Thr Gly Asp Phe Asp
65                  70                  75                  80
```

```
Leu His Leu Leu Lys Val Ser Glu Gly Thr Thr Ile Leu Leu Asn Cys
                85                  90                  95

Thr Gly Gln Val Lys Gly Arg Lys Pro Ala Ala Leu Gly Glu Ala Gln
            100                 105                 110

Pro Thr Lys Ser Leu Glu Glu Asn Lys Ser Leu Lys Glu Gln Lys Lys
            115                 120                 125

Leu Asn Asp Leu Cys Phe Leu Lys Arg Leu Leu Gln Glu Ile Lys Thr
130                 135                 140

Cys Trp Asn Lys Ile Leu Met Gly Thr Lys Glu His
145                 150                 155

<210> SEQ ID NO 21
<211> LENGTH: 398
<212> TYPE: PRT
<213> ORGANISM: Artificial Sequence
<220> FEATURE:
<223> OTHER INFORMATION: amino acid sequence of modified IL-7(M) fused
      hyFc

<400> SEQUENCE: 21

Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
                20                  25                  30

Ser Asn Cys Leu Asn Asn Glu Phe Asn Phe Lys Arg His Ile Cys
            35                  40                  45

Asp Ala Asn Lys Glu Gly Met Phe Leu Phe Arg Ala Ala Arg Lys Leu
        50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
            115                 120                 125

Leu Cys Phe Leu Lys Arg Leu Leu Gln Glu Ile Lys Thr Cys Trp Asn
130                 135                 140

Lys Ile Leu Met Gly Thr Lys Glu His Arg Asn Thr Gly Arg Gly Gly
145                 150                 155                 160

Glu Glu Lys Lys Lys Glu Lys Glu Lys Glu Glu Gln Glu Glu Arg Glu
            165                 170                 175

Thr Lys Thr Pro Glu Cys Pro Ser His Thr Gln Pro Leu Gly Val Phe
            180                 185                 190

Leu Phe Pro Pro Lys Pro Lys Asp Thr Leu Met Ile Ser Arg Thr Pro
            195                 200                 205

Glu Val Thr Cys Val Val Val Asp Val Ser Gln Glu Asp Pro Glu Val
            210                 215                 220

Gln Phe Asn Trp Tyr Val Asp Gly Val Glu Val His Asn Ala Lys Thr
225                 230                 235                 240

Lys Pro Arg Glu Glu Gln Phe Asn Ser Thr Tyr Arg Val Val Ser Val
            245                 250                 255

Leu Thr Val Leu His Gln Asp Trp Leu Asn Gly Lys Glu Tyr Lys Cys
            260                 265                 270

Lys Val Ser Asn Lys Gly Leu Pro Ser Ser Ile Glu Lys Thr Ile Ser
            275                 280                 285
```

```
Lys Ala Lys Gly Gln Pro Arg Glu Pro Gln Val Tyr Thr Leu Pro Pro
        290                 295                 300
Ser Gln Glu Glu Met Thr Lys Asn Gln Val Ser Leu Thr Cys Leu Val
305                 310                 315                 320
Lys Gly Phe Tyr Pro Ser Asp Ile Ala Val Glu Trp Glu Ser Asn Gly
                325                 330                 335
Gln Pro Glu Asn Asn Tyr Lys Thr Thr Pro Val Leu Asp Ser Asp
            340                 345                 350
Gly Ser Phe Phe Leu Tyr Ser Arg Leu Thr Val Asp Lys Ser Arg Trp
        355                 360                 365
Gln Glu Gly Asn Val Phe Ser Cys Ser Val Met His Glu Ala Leu His
        370                 375                 380
Asn His Tyr Thr Gln Lys Ser Leu Ser Leu Ser Leu Gly Lys
385                 390                 395

<210> SEQ ID NO 22
<211> LENGTH: 399
<212> TYPE: PRT
<213> ORGANISM: Artificial Sequence
<220> FEATURE:
<223> OTHER INFORMATION: amino acid sequence of modified IL-7(MM) fused
      hyFc

<400> SEQUENCE: 22

Met Met Asp Cys Asp Ile Glu Gly Lys Asp Gly Lys Gln Tyr Glu Ser
1               5                   10                  15
Val Leu Met Val Ser Ile Asp Gln Leu Leu Asp Ser Met Lys Glu Ile
            20                  25                  30
Gly Ser Asn Cys Leu Asn Asn Glu Phe Asn Phe Phe Lys Arg His Ile
        35                  40                  45
Cys Asp Ala Asn Lys Glu Gly Met Phe Leu Phe Arg Ala Ala Arg Lys
    50                  55                  60
Leu Arg Gln Phe Leu Lys Met Asn Ser Thr Gly Asp Phe Asp Leu His
65                  70                  75                  80
Leu Leu Lys Val Ser Glu Gly Thr Thr Ile Leu Leu Asn Cys Thr Gly
                85                  90                  95
Gln Val Lys Gly Arg Lys Pro Ala Ala Leu Gly Glu Ala Gln Pro Thr
            100                 105                 110
Lys Ser Leu Glu Glu Asn Lys Ser Leu Lys Glu Gln Lys Lys Leu Asn
        115                 120                 125
Asp Leu Cys Phe Leu Lys Arg Leu Leu Gln Glu Ile Lys Thr Cys Trp
    130                 135                 140
Asn Lys Ile Leu Met Gly Thr Lys Glu His Arg Asn Thr Gly Arg Gly
145                 150                 155                 160
Gly Glu Glu Lys Lys Lys Glu Lys Glu Glu Gln Glu Glu Arg
                165                 170                 175
Glu Thr Lys Thr Pro Glu Cys Pro Ser His Thr Gln Pro Leu Gly Val
            180                 185                 190
Phe Leu Phe Pro Pro Lys Pro Lys Asp Thr Leu Met Ile Ser Arg Thr
        195                 200                 205
Pro Glu Val Thr Cys Val Val Val Asp Val Ser Gln Glu Asp Pro Glu
    210                 215                 220
Val Gln Phe Asn Trp Tyr Val Asp Gly Val Glu Val His Asn Ala Lys
225                 230                 235                 240
Thr Lys Pro Arg Glu Glu Gln Phe Asn Ser Thr Tyr Arg Val Val Ser
```

```
                245                 250                 255
Val Leu Thr Val Leu His Gln Asp Trp Leu Asn Gly Lys Glu Tyr Lys
            260                 265                 270

Cys Lys Val Ser Asn Lys Gly Leu Pro Ser Ser Ile Glu Lys Thr Ile
        275                 280                 285

Ser Lys Ala Lys Gly Gln Pro Arg Glu Pro Gln Val Tyr Thr Leu Pro
    290                 295                 300

Pro Ser Gln Glu Glu Met Thr Lys Asn Gln Val Ser Leu Thr Cys Leu
305                 310                 315                 320

Val Lys Gly Phe Tyr Pro Ser Asp Ile Ala Val Glu Trp Glu Ser Asn
                325                 330                 335

Gly Gln Pro Glu Asn Asn Tyr Lys Thr Thr Pro Pro Val Leu Asp Ser
            340                 345                 350

Asp Gly Ser Phe Phe Leu Tyr Ser Arg Leu Thr Val Asp Lys Ser Arg
        355                 360                 365

Trp Gln Glu Gly Asn Val Phe Ser Cys Ser Val Met His Glu Ala Leu
    370                 375                 380

His Asn His Tyr Thr Gln Lys Ser Leu Ser Leu Ser Leu Gly Lys
385                 390                 395

<210> SEQ ID NO 23
<211> LENGTH: 400
<212> TYPE: PRT
<213> ORGANISM: Artificial Sequence
<220> FEATURE:
<223> OTHER INFORMATION: amino acid sequence of modified IL-7(MMM) fused
      hyFc

<400> SEQUENCE: 23

Met Met Met Asp Cys Asp Ile Glu Gly Lys Asp Gly Lys Gln Tyr Glu
1               5                   10                  15

Ser Val Leu Met Val Ser Ile Asp Gln Leu Leu Asp Ser Met Lys Glu
            20                  25                  30

Ile Gly Ser Asn Cys Leu Asn Asn Glu Phe Asn Phe Phe Lys Arg His
        35                  40                  45

Ile Cys Asp Ala Asn Lys Glu Gly Met Phe Leu Phe Arg Ala Ala Arg
    50                  55                  60

Lys Leu Arg Gln Phe Leu Lys Met Asn Ser Thr Gly Asp Phe Asp Leu
65                  70                  75                  80

His Leu Leu Lys Val Ser Glu Gly Thr Thr Ile Leu Leu Asn Cys Thr
                85                  90                  95

Gly Gln Val Lys Gly Arg Lys Pro Ala Ala Leu Gly Glu Ala Gln Pro
            100                 105                 110

Thr Lys Ser Leu Glu Glu Asn Lys Ser Leu Lys Glu Gln Lys Lys Leu
        115                 120                 125

Asn Asp Leu Cys Phe Leu Lys Arg Leu Leu Gln Glu Ile Lys Thr Cys
    130                 135                 140

Trp Asn Lys Ile Leu Met Gly Thr Lys Glu His Arg Asn Thr Gly Arg
145                 150                 155                 160

Gly Gly Glu Glu Lys Lys Glu Lys Glu Lys Glu Glu Gln Glu Glu
                165                 170                 175

Arg Glu Thr Lys Thr Pro Glu Cys Pro Ser His Thr Gln Pro Leu Gly
            180                 185                 190

Val Phe Leu Phe Pro Pro Lys Pro Lys Asp Thr Leu Met Ile Ser Arg
        195                 200                 205
```

```
Thr Pro Glu Val Thr Cys Val Val Val Asp Val Ser Gln Glu Asp Pro
    210                 215                 220
Glu Val Gln Phe Asn Trp Tyr Val Asp Gly Val Glu Val His Asn Ala
225                 230                 235                 240
Lys Thr Lys Pro Arg Glu Glu Gln Phe Asn Ser Thr Tyr Arg Val Val
                245                 250                 255
Ser Val Leu Thr Val Leu His Gln Asp Trp Leu Asn Gly Lys Glu Tyr
            260                 265                 270
Lys Cys Lys Val Ser Asn Lys Gly Leu Pro Ser Ser Ile Glu Lys Thr
        275                 280                 285
Ile Ser Lys Ala Lys Gly Gln Pro Arg Glu Pro Gln Val Tyr Thr Leu
    290                 295                 300
Pro Pro Ser Gln Glu Glu Met Thr Lys Asn Gln Val Ser Leu Thr Cys
305                 310                 315                 320
Leu Val Lys Gly Phe Tyr Pro Ser Asp Ile Ala Val Glu Trp Glu Ser
                325                 330                 335
Asn Gly Gln Pro Glu Asn Asn Tyr Lys Thr Thr Pro Pro Val Leu Asp
            340                 345                 350
Ser Asp Gly Ser Phe Phe Leu Tyr Ser Arg Leu Thr Val Asp Lys Ser
        355                 360                 365
Arg Trp Gln Glu Gly Asn Val Phe Ser Cys Ser Val Met His Glu Ala
    370                 375                 380
Leu His Asn His Tyr Thr Gln Lys Ser Leu Ser Leu Ser Leu Gly Lys
385                 390                 395                 400

<210> SEQ ID NO 24
<211> LENGTH: 400
<212> TYPE: PRT
<213> ORGANISM: Artificial Sequence
<220> FEATURE:
<223> OTHER INFORMATION: amino acid sequence of modified IL-7(MGM) fused
      hyFc

<400> SEQUENCE: 24

Met Gly Met Asp Cys Asp Ile Glu Gly Lys Asp Gly Lys Gln Tyr Glu
1               5                   10                  15
Ser Val Leu Met Val Ser Ile Asp Gln Leu Leu Asp Ser Met Lys Glu
                20                  25                  30
Ile Gly Ser Asn Cys Leu Asn Asn Glu Phe Asn Phe Phe Lys Arg His
            35                  40                  45
Ile Cys Asp Ala Asn Lys Glu Gly Met Phe Leu Phe Arg Ala Ala Arg
        50                  55                  60
Lys Leu Arg Gln Phe Leu Lys Met Asn Ser Thr Gly Asp Phe Asp Leu
65                  70                  75                  80
His Leu Leu Lys Val Ser Glu Gly Thr Thr Ile Leu Leu Asn Cys Thr
                85                  90                  95
Gly Gln Val Lys Gly Arg Lys Pro Ala Ala Leu Gly Glu Ala Gln Pro
            100                 105                 110
Thr Lys Ser Leu Glu Glu Asn Lys Ser Leu Lys Glu Gln Lys Lys Leu
        115                 120                 125
Asn Asp Leu Cys Phe Leu Lys Arg Leu Leu Gln Glu Ile Lys Thr Cys
    130                 135                 140
Trp Asn Lys Ile Leu Met Gly Thr Lys Glu His Arg Asn Thr Gly Arg
145                 150                 155                 160
Gly Gly Glu Glu Lys Lys Lys Glu Lys Glu Lys Glu Glu Gln Glu Glu
                165                 170                 175
```

-continued

```
Arg Glu Thr Lys Thr Pro Glu Cys Pro Ser His Thr Gln Pro Leu Gly
            180                 185                 190

Val Phe Leu Phe Pro Pro Lys Pro Lys Asp Thr Leu Met Ile Ser Arg
        195                 200                 205

Thr Pro Glu Val Thr Cys Val Val Val Asp Val Ser Gln Glu Asp Pro
    210                 215                 220

Glu Val Gln Phe Asn Trp Tyr Val Asp Gly Val Glu Val His Asn Ala
225                 230                 235                 240

Lys Thr Lys Pro Arg Glu Gln Phe Asn Ser Thr Tyr Arg Val Val
                245                 250                 255

Ser Val Leu Thr Val Leu His Gln Asp Trp Leu Asn Gly Lys Glu Tyr
            260                 265                 270

Lys Cys Lys Val Ser Asn Lys Gly Leu Pro Ser Ser Ile Glu Lys Thr
        275                 280                 285

Ile Ser Lys Ala Lys Gly Gln Pro Arg Glu Pro Gln Val Tyr Thr Leu
    290                 295                 300

Pro Pro Ser Gln Glu Glu Met Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
            340                 345                 350

Ser Asp Gly Ser Phe Phe Leu Tyr Ser Arg Leu Thr Val Asp Lys Ser
        355                 360                 365

Arg Trp Gln Glu Gly Asn Val Phe Ser Cys Ser Val Met His Glu Ala
    370                 375                 380

Leu His Asn His Tyr Thr Gln Lys Ser Leu Ser Leu Ser Leu Gly Lys
385                 390                 395                 400
```

<210> SEQ ID NO 25
<211> LENGTH: 401
<212> TYPE: PRT
<213> ORGANISM: Artificial Sequence
<220> FEATURE:
<223> OTHER INFORMATION: amino acid sequence of modified IL-7(MMMM)
    fused hyFc

<400> SEQUENCE: 25

```
Met Met Met Met Asp Cys Asp Ile Glu Gly Lys Asp Gly Lys Gln Tyr
1               5                   10                  15

Glu Ser Val Leu Met Val Ser Ile Asp Gln Leu Leu Asp Ser Met Lys
            20                  25                  30

Glu Ile Gly Ser Asn Cys Leu Asn Asn Glu Phe Asn Phe Lys Arg
        35                  40                  45

His Ile Cys Asp Ala Asn Lys Glu Gly Met Phe Leu Phe Arg Ala Ala
    50                  55                  60

Arg Lys Leu Arg Gln Phe Leu Lys Met Asn Ser Thr Gly Asp Phe Asp
65                  70                  75                  80

Leu His Leu Leu Lys Val Ser Glu Gly Thr Thr Ile Leu Leu Asn Cys
                85                  90                  95

Thr Gly Gln Val Lys Gly Arg Lys Pro Ala Ala Leu Gly Glu Ala Gln
            100                 105                 110

Pro Thr Lys Ser Leu Glu Glu Asn Lys Ser Leu Lys Glu Gln Lys Lys
        115                 120                 125

Leu Asn Asp Leu Cys Phe Leu Lys Arg Leu Leu Gln Glu Ile Lys Thr
```

```
            130                 135                 140
Cys Trp Asn Lys Ile Leu Met Gly Thr Lys Glu His Arg Asn Thr Gly
145                 150                 155                 160

Arg Gly Gly Glu Glu Lys Lys Lys Glu Lys Glu Lys Glu Glu Gln Glu
                165                 170                 175

Glu Arg Glu Thr Lys Thr Pro Glu Cys Pro Ser His Thr Gln Pro Leu
            180                 185                 190

Gly Val Phe Leu Phe Pro Pro Lys Pro Lys Asp Thr Leu Met Ile Ser
                195                 200                 205

Arg Thr Pro Glu Val Thr Cys Val Val Val Asp Val Ser Gln Glu Asp
210                 215                 220

Pro Glu Val Gln Phe Asn Trp Tyr Val Asp Gly Val Glu Val His Asn
225                 230                 235                 240

Ala Lys Thr Lys Pro Arg Glu Glu Gln Phe Asn Ser Thr Tyr Arg Val
                245                 250                 255

Val Ser Val Leu Thr Val Leu His Gln Asp Trp Leu Asn Gly Lys Glu
                260                 265                 270

Tyr Lys Cys Lys Val Ser Asn Lys Gly Leu Pro Ser Ser Ile Glu Lys
            275                 280                 285

Thr Ile Ser Lys Ala Lys Gly Gln Pro Arg Glu Pro Gln Val Tyr Thr
            290                 295                 300

Leu Pro Pro Ser Gln Glu Glu Met Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
                340                 345                 350

Asp Ser Asp Gly Ser Phe Phe Leu Tyr Ser Arg Leu Thr Val Asp Lys
            355                 360                 365

Ser Arg Trp Gln Glu Gly Asn Val Phe Ser Cys Ser Val Met His Glu
            370                 375                 380

Ala Leu His Asn His Tyr Thr Gln Lys Ser Leu Ser Leu Ser Leu Gly
385                 390                 395                 400

Lys

<210> SEQ ID NO 26
<211> LENGTH: 397
<212> TYPE: PRT
<213> ORGANISM: Artificial Sequence
<220> FEATURE:
<223> OTHER INFORMATION: amino acid sequence of human IL-7 fused hyFc

<400> SEQUENCE: 26

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
                20                  25                  30

Asn Cys Leu Asn Asn Glu Phe Asn Phe Phe Lys Arg His Ile Cys Asp
            35                  40                  45

Ala Asn Lys Glu Gly Met Phe Leu Phe Arg Ala Ala Arg Lys Leu Arg
        50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95
```

```
Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
            115                 120                 125

Cys Phe Leu Lys Arg Leu Leu Gln Glu Ile Lys Thr Cys Trp Asn Lys
130                 135                 140

Ile Leu Met Gly Thr Lys Glu His Arg Asn Thr Gly Arg Gly Gly Glu
145                 150                 155                 160

Glu Lys Lys Lys Glu Lys Glu Lys Glu Gln Glu Glu Arg Glu Thr
                165                 170                 175

Lys Thr Pro Glu Cys Pro Ser His Thr Gln Pro Leu Gly Val Phe Leu
            180                 185                 190

Phe Pro Pro Lys Pro Lys Asp Thr Leu Met Ile Ser Arg Thr Pro Glu
            195                 200                 205

Val Thr Cys Val Val Val Asp Val Ser Gln Glu Asp Pro Glu Val Gln
210                 215                 220

Phe Asn Trp Tyr Val Asp Gly Val Glu Val His Asn Ala Lys Thr Lys
225                 230                 235                 240

Pro Arg Glu Glu Gln Phe Asn Ser Thr Tyr Arg Val Val Ser Val Leu
            245                 250                 255

Thr Val Leu His Gln Asp Trp Leu Asn Gly Lys Glu Tyr Lys Cys Lys
            260                 265                 270

Val Ser Asn Lys Gly Leu Pro Ser Ser Ile Glu Lys Thr Ile Ser Lys
            275                 280                 285

Ala Lys Gly Gln Pro Arg Glu Pro Gln Val Tyr Thr Leu Pro Pro Ser
290                 295                 300

Gln Glu Glu Met Thr Lys Asn Gln Val Ser Leu Thr Cys Leu Val Lys
305                 310                 315                 320

Gly Phe Tyr Pro Ser Asp Ile Ala Val Glu Trp Glu Ser Asn Gly Gln
            325                 330                 335

Pro Glu Asn Asn Tyr Lys Thr Thr Pro Pro Val Leu Asp Ser Asp Gly
            340                 345                 350

Ser Phe Phe Leu Tyr Ser Arg Leu Thr Val Asp Lys Ser Arg Trp Gln
            355                 360                 365

Glu Gly Asn Val Phe Ser Cys Ser Val Met His Glu Ala Leu His Asn
            370                 375                 380

His Tyr Thr Gln Lys Ser Leu Ser Leu Ser Leu Gly Lys
385                 390                 395

<210> SEQ ID NO 27
<211> LENGTH: 395
<212> TYPE: PRT
<213> ORGANISM: Artificial Sequence
<220> FEATURE:
<223> OTHER INFORMATION: amino acid sequence of human IL-7 fused
      nonlytic mouse Fc

<400> SEQUENCE: 27

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
            35                  40                  45

Ala Asn Lys Glu Gly Met Phe Leu Phe Arg Ala Ala Arg Lys Leu Arg
```

```
        50                  55                  60
Gln Phe Leu Lys Met Asn Ser Thr Gly Asp Phe Asp Leu His Leu Leu
 65                  70                  75                  80

Lys Val Ser Glu Gly Thr Thr Ile Leu Leu Asn Cys Thr Gly Gln Val
                 85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
130                 135                 140

Ile Leu Met Gly Thr Lys Glu His Ala Ser Ala Glu Pro Arg Gly Pro
145                 150                 155                 160

Thr Ile Lys Pro Cys Pro Pro Cys Lys Cys Pro Ala Pro Asn Leu Glu
                165                 170                 175

Gly Gly Pro Ser Val Phe Ile Phe Pro Pro Lys Ile Lys Asp Val Leu
            180                 185                 190

Met Ile Ser Leu Ser Pro Ile Val Thr Cys Val Val Asp Val Ser
        195                 200                 205

Glu Asp Asp Pro Asp Val Gln Ile Ser Trp Phe Val Asn Asn Val Glu
210                 215                 220

Val His Thr Ala Gln Thr Gln Thr His Arg Glu Asp Tyr Asn Ser Thr
225                 230                 235                 240

Leu Arg Val Val Ser Ala Leu Pro Ile Gln His Gln Asp Trp Met Ser
                245                 250                 255

Gly Lys Ala Phe Ala Cys Ala Val Asn Asn Lys Asp Leu Pro Ala Pro
            260                 265                 270

Ile Glu Arg Thr Ile Ser Lys Pro Lys Gly Ser Val Arg Ala Pro Gln
        275                 280                 285

Val Tyr Val Leu Pro Pro Glu Glu Glu Met Thr Lys Lys Gln Val
290                 295                 300

Thr Leu Thr Cys Met Val Thr Asp Phe Met Pro Glu Asp Ile Tyr Val
305                 310                 315                 320

Glu Trp Thr Asn Asn Gly Lys Thr Glu Leu Asn Tyr Lys Asn Thr Glu
                325                 330                 335

Pro Val Leu Asp Ser Asp Gly Ser Tyr Phe Met Tyr Ser Lys Leu Arg
            340                 345                 350

Val Glu Lys Lys Asn Trp Val Glu Arg Asn Ser Tyr Ser Cys Ser Val
        355                 360                 365

Val His Glu Gly Leu His Asn His His Thr Thr Lys Ser Phe Ser Arg
370                 375                 380

Thr Pro Gly Lys Gly Gly Gly Asn Ser Gly Ser
385                 390                 395

<210> SEQ ID NO 28
<211> LENGTH: 531
<212> TYPE: DNA
<213> ORGANISM: Artificial Sequence
<220> FEATURE:
<223> OTHER INFORMATION: nucleotide sequence of human IL-7

<400> SEQUENCE: 28
atgttccacg tgagcttcag gtacatcttc ggcctgccac ccctgatcct ggtgctgctg     60
cctgtggcca gctccgactg cgacatcgag ggaaaagacg gcaagcagta cgaaagcgtg    120
```

```
ctgatggtgt ccatcgacca gctgctggat tctatgaagg agattgggag taactgcctg      180
aacaatgagt tcaacttctt caaacggcac atttgtgatg ccaacaagga gggaatgttc      240
ctgtttcggg ccgctagaaa actgaggcag ttcctgaaga tgaacagcac cggagacttt      300
gatctgcatc tgctgaaagt gtctgagggc accacaatcc tgctgaactg cactgggcag      360
gtgaaaggaa ggaagcctgc cgctctggga gaggctcagc caaccaagtc actggaggaa      420
aacaaaagcc tgaaggaaca agagaaactg aatgacctgt gctttctgaa acggctgctg      480
caggagatca aacatgttg gaacaagatt ctgatgggca aaaggaaca c                 531

<210> SEQ ID NO 29
<211> LENGTH: 534
<212> TYPE: DNA
<213> ORGANISM: Artificial Sequence
<220> FEATURE:
<223> OTHER INFORMATION: nucleotide sequence of modified IL-7(M)

<400> SEQUENCE: 29
atgttccacg tgagcttcag atacatcttc ggcctgcccc cctgatcct ggtgctgctg       60 cccgtggcca gcagcatgga ctgcgacatc gagggcaagg acggcaagca gtacgagagc      120
gtgctgatgg tgagcatcga ccagctgctg acagcatga aggagatcgg cagcaactgc      180
ctgaacaacg agttcaactt cttcaagaga cacatctgcg acgccaacaa ggagggcatg      240
ttcctgttca gagccgccag aaagctgaga cagttcctga gatgaacag caccggcgac      300 ttcgacctgc acctgctgaa ggtgagcgag ggcacaacca tcctgctgaa ctgcaccggc      360
caggtgaagg gcagaaagcc cgccgccctg ggcgaggccc agcccaccaa gagcctggag      420
gagaacaaga gcctgaagga gcagaagaag ctgaacgacc tgtgcttcct gaagagactg      480
ctgcaggaga tcaagacctg ctggaacaag atcctgatgg gcaccaagga gcac           534

<210> SEQ ID NO 30
<211> LENGTH: 537
<212> TYPE: DNA
<213> ORGANISM: Artificial Sequence
<220> FEATURE:
<223> OTHER INFORMATION: nucleotide sequence of modified IL-7(MM)

<400> SEQUENCE: 30
atgttccacg tgagcttcag atacatcttc ggcctgcccc cctgatcct ggtgctgctg       60 cccgtggcca gcagcatgat ggactgcgac atcgagggca aggacggcaa gcagtacgag      120
agcgtgctga tggtgagcat cgaccagctg ctggacagca tgaaggagat cggcagcaac      180
tgcctgaaca acgagttcaa cttcttcaag agacacatct gcgacgccaa caaggagggc      240
atgttcctgt tcagagccgc cagaaagctg agacagttcc tgaagatgaa cagcaccggc      300
gacttcgacc tgcacctgct gaaggtgagc gagggcacaa ccatcctgct gaactgcacc      360
ggccaggtga agggcagaaa gcccgccgcc ctgggcgagg cccagcccac caagagcctg      420
gaggagaaca agagcctgaa ggagcagaag aagctgaacg acctgtgctt cctgaagaga      480
ctgctgcagg agatcaagac ctgctggaac aagatcctga tgggcaccaa ggagcac        537

<210> SEQ ID NO 31
<211> LENGTH: 540
<212> TYPE: DNA
<213> ORGANISM: Artificial Sequence
<220> FEATURE:
<223> OTHER INFORMATION: nucleotide sequence of modified IL-7(MMM)

<400> SEQUENCE: 31
```

```
atgttccacg tgagcttcag atacatcttc ggcctgcccc ccctgatcct ggtgctgctg        60
cccgtggcca gcagcatgat gatggactgc gacatcgagg gcaaggacgg caagcagtac       120
gagagcgtgc tgatggtgag catcgaccag ctgctggaca gcatgaagga gatcggcagc       180
aactgcctga caacgagtt caacttcttc aagagacaca tctgcgacgc caacaaggag        240
ggcatgttcc tgttcagagc cgccagaaag ctgagacagt tcctgaagat gaacagcacc       300
ggcgacttcg acctgcacct gctgaaggtg agcgagggca caaccatcct gctgaactgc       360
accggccagg tgaagggcag aaagcccgcc gccctgggcg aggcccagcc caccaagagc       420
ctggaggaga acaagagcct gaaggagcag aagaagctga cgacctgtg cttcctgaag         480 agactgctgc aggagatcaa gacctgctgg aacaagatcc tgatgggcac caaggagcac       540
```

<210> SEQ ID NO 32
<211> LENGTH: 540
<212> TYPE: DNA
<213> ORGANISM: Artificial Sequence
<220> FEATURE:
<223> OTHER INFORMATION: nucleotide sequence of modified IL-7(MGM)

<400> SEQUENCE: 32

```
atgttccacg tgagcttcag gtacatcttc ggcctgccac ccctgatcct ggtgctgctg        60
cctgtggcca gctccatggg gatggactgc gacatcgagg gaaaagacgg caagcagtac       120
gaaagcgtgc tgatggtgtc catcgaccag ctgctggatt ctatgaagga gattgggagt       180
aactgcctga caatgagtt caacttcttc aaacggcaca tttgtgatgc caacaaggag         240
ggaatgttcc tgtttcgggc cgctagaaaa ctgaggcagt tcctgaagat gaacagcacc       300
ggagactttg atctgcatct gctgaaagtg tctgagggca ccacaatcct gctgaactgc       360
actgggcagg tgaaaggaag gaagcctgcc gctctgggag aggctcagcc aaccaagtca       420
ctggaggaaa acaaaagcct gaaggaacag aagaaactga atgacctgtg ctttctgaaa       480
cggctgctgc aggagatcaa acatgttgg aacaagattc tgatgggcac caaggagcac         540
```

<210> SEQ ID NO 33
<211> LENGTH: 540
<212> TYPE: DNA
<213> ORGANISM: Artificial Sequence
<220> FEATURE:
<223> OTHER INFORMATION: nucleotide sequence of modified IL-7(DDD)

<400> SEQUENCE: 33

```
atgttccacg tgagcttcag atacatcttc ggcctgcccc ccctgatcct ggtgctgctg        60
cccgtggcca gcgcgacga tgacgactgc gacatcgagg gcaaggacgg caagcagtac        120
gagagcgtgc tgatggtgag catcgaccag ctgctggaca gcatgaagga gatcggcagc       180
aactgcctga caacgagtt caacttcttc aagagacaca tctgcgacgc caacaaggag        240
ggcatgttcc tgttcagagc cgccagaaag ctgagacagt tcctgaagat gaacagcacc       300
ggcgacttcg acctgcacct gctgaaggtg agcgagggca caaccatcct gctgaactgc       360
accggccagg tgaagggcag aaagcccgcc gccctgggcg aggcccagcc caccaagagc       420
ctggaggaga acaagagcct gaaggagcag aagaagctga cgacctgtg cttcctgaag         480 agactgctgc aggagatcaa gacctgctgg aacaagatcc tgatgggcac caaggagcac       540
```

<210> SEQ ID NO 34
<211> LENGTH: 543
<212> TYPE: DNA

<213> ORGANISM: Artificial Sequence
<220> FEATURE:
<223> OTHER INFORMATION: nucleotide sequence of modified IL-7(MMMM)

<400> SEQUENCE: 34

```
atgttccacg tgagcttcag atacatcttc ggcctgcccc ccctgatcct ggtgctgctg      60
cccgtggcca gcagcatgat gatgatggac tgcgacatcg agggcaagga cggcaagcag     120
tacgagagcg tgctgatggt gagcatcgac cagctgctgg acagcatgaa ggagatcggc     180
agcaactgcc tgaacaacga gttcaacttc ttcaagagac acatctgcga cgccaacaag     240
gagggcatgt tcctgttcag agccgccaga aagctgagac agttcctgaa gatgaacagc     300
accggcgact tcgacctgca cctgctgaag gtgagcgagg gcacaaccat cctgctgaac     360
tgcaccggcc aggtgaaggg cagaaagccc gccgccctgg gcgaggccca gcccaccaag     420
agcctggagg agaacaagag cctgaaggag cagaagaagc tgaacgacct gtgcttcctg     480
aagagactgc tgcaggagat caagacctgc tggaacaaga tcctgatggg caccaaggag     540
cac                                                                   543
```

<210> SEQ ID NO 35
<211> LENGTH: 1284
<212> TYPE: DNA
<213> ORGANISM: Artificial Sequence
<220> FEATURE:
<223> OTHER INFORMATION: nucleotide sequence of modified IL-7(M) fused hyFc

<400> SEQUENCE: 35

```
atgttccacg tgagcttcag atacatcttc ggcctgcccc ccctgatcct ggtgctgctg      60
cccgtggcca gcagcatgga ctgcgacatc gagggcaagg acggcaagca gtacgagagc     120
gtgctgatgg tgagcatcga ccagctgctg gacagcatga aggagatcgg cagcaactgc     180
ctgaacaacg agttcaactt cttcaagaga cacatctgcg acgccaacaa ggagggcatg     240
ttcctgttca gagccgccag aaagctgaga cagttcctga gatgaacag caccggcgac     300
ttcgacctgc acctgctgaa ggtgagcgag ggcacaacca tcctgctgaa ctgcaccggc     360
caggtgaagg gcagaaagcc cgccgccctg ggcgaggccc agcccaccaa gagcctggag     420
gagaacaaga gcctgaagga gcagaagaag ctgaacgacc tgtgcttcct gaagagactg     480
ctgcaggaga tcaagacctg ctggaacaag atcctgatgg gcaccaagga gcacaggaac     540
acaggcagag cggcgagga agaagaagag gaaggagag ggaggagca ggaggaaaga     600
gagaccaaga ccccccagtg ccccagccac acccagcccc tgggcgtgtt cctgttccct     660
cccaagccca aggacaccct gatgatcagc agaacccccg aggtgacctg cgtggtcgtg     720
gatgtgagcc aggaagatcc cgaagtgcag ttcaactggt acgtggatgg cgtggaagtg     780
cacaacgcca agaccaagcc cagagaagag cagttcaact ccacctacag agtggtgagc     840
gtgctgaccg tgctgcacca ggactggctg aacggcaagg agtacaagtg caaggtgtcc     900
aacaaaggcc tgcccagctc catcgagaag accatcagca agccaaagg ccagcccaga     960
gaacccagg tgtacaccct gcctcccagc caggaagaga tgaccaagaa ccaggtgtcc    1020
ctgacctgcc tggtgaaagg cttctacccc agcgacatcg ccgtggagtg ggaaagcaac    1080
ggccagcccg agaacaatta caagacaacc cctcccgtgc tggatagcga tggcagcttc    1140
tttctgtaca gcagactgac cgtggacaag agcagatggc aggaaggcaa cgtgttcagc    1200
tgcagcgtga tgcacgaagc cctgcacaac cactacaccc agaagagcct gtccctgagc    1260
```

```
ctgggcaagt gactcgagtc taga                                          1284
```

<210> SEQ ID NO 36
<211> LENGTH: 1272
<212> TYPE: DNA
<213> ORGANISM: Artificial Sequence
<220> FEATURE:
<223> OTHER INFORMATION: nucleotide sequence of modified IL-7(MM) fused
      hyFc

<400> SEQUENCE: 36

```
atgttccacg tgagcttcag atacatcttc ggcctgcccc ccctgatcct ggtgctgctg    60
cccgtggcca gcagcatgat ggactgcgac atcgagggca aggacggcaa gcagtacgag   120
agcgtgctga tggtgagcat cgaccagctg ctggacagca tgaaggagat cggcagcaac   180
tgcctgaaca acgagttcaa cttcttcaag agacacatct cgacgccaa caaggagggc   240
atgttcctgt tcagagccgc cagaaagctg agacagttcc tgaagatgaa cagcaccggc   300
gacttcgacc tgcacctgct gaaggtgagc gagggcacaa ccatcctgct gaactgcacc   360
ggccaggtga agggcagaaa gcccgccgcc ctgggcgagg cccagcccac caagagcctg   420
gaggagaaca gagcctgaa ggagcagaag aagctgaacg acctgtgctt cctgaagaga   480
ctgctgcagg agatcaagac ctgctggaac aagatcctga tgggcaccaa ggagcacagg   540
aacacaggca gaggcggcga ggagaagaag aaggagaagg agaaggagga gcaggaggaa   600
agagagacca gaccccga gtgccccagc cacacccagc ccctgggcgt gttcctgttc   660
cctcccaagc caaggacac cctgatgatc agcagaaccc ccgaggtgac ctgcgtggtc   720
gtggatgtga gccaggaaga tcccgaagtg cagttcaact ggtacgtgga tggcgtggaa   780
gtgcacaacg ccaagaccaa gcccagagaa gagcagttca actccaccta cagagtggtg   840
agcgtgctga ccgtgctgca ccaggactgg ctgaacggca ggagtacaa gtgcaaggtg   900
tccaacaaag gcctgcccag ctccatcgag aagaccatca gcaaagccaa aggccagccc   960
agagaaccccc aggtgtacac cctgcctccc agccaggaag atgaccaa gaaccaggtg  1020
tccctgacct gcctggtgaa aggcttctac cccagcgaca tcgccgtgga gtgggaaagc  1080
aacggccagc ccgagaacaa ttacaagaca accctcccg tgctggatag cgatggcagc  1140
ttctttctgt acagcagact gaccgtggac aagagcagat ggcaggaagg caacgtgttc  1200
agctgcagcg tgatgcacga agccctgcac aaccactaca cccagaagag cctgtccctg  1260
agcctgggca ag                                                      1272
```

<210> SEQ ID NO 37
<211> LENGTH: 1275
<212> TYPE: DNA
<213> ORGANISM: Artificial Sequence
<220> FEATURE:
<223> OTHER INFORMATION: nucleotide sequence of modified IL-7(MMM) fused
      hyFc

<400> SEQUENCE: 37

```
atgttccacg tgagcttcag atacatcttc ggcctgcccc ccctgatcct ggtgctgctg    60
cccgtggcca gcagcatgat gatggactgc gacatcgagg gcaaggacgg caagcagtac   120
gagagcgtgc tgatggtgag catcgaccag ctgctggaca gcatgaagga gatcggcagc   180
aactgcctga caacgagtt caacttcttc aagagacaca tctgcgacgc caacaaggag   240
ggcatgttcc tgttcagagc cgccagaaag ctgagacagt tcctgaagat gaacagcacc   300
ggcgacttcg acctgcacct gctgaaggtg agcgagggca accatcct gctgaactgc   360
```

```
accggccagg tgaagggcag aaagcccgcc gccctgggcg aggcccagcc caccaagagc      420
ctggaggaga caagagcct gaaggagcag aagaagctga cgacctgtg cttcctgaag       480 agactgctgc aggagatcaa gacctgctgg aacaagatcc tgatgggcac caaggagcac    540
aggaacacag gcagaggcgg cgaggagaag aagaaggaga ggagaaggag ggagcaggag    600
gaaagagaga ccaagacccc cgagtgcccc agccacaccc agcccctggg cgtgttcctg    660
ttccctccca agcccaagga caccctgatg atcagcagaa cccccgaggt gacctgcgtg    720
gtcgtggatg tgagccagga agatcccgaa gtgcagttca actggtacgt ggatggcgtg    780
gaagtgcaca cgccaagac caagcccaga gaagagcagt tcaactccac ctacagagtg     840
gtgagcgtgc tgaccgtgct gcaccaggac tggctgaacg gcaaggagta caagtgcaag    900
gtgtccaaca aggcctgcc cagctccatc gagaagacca tcagcaaagc caaggccag     960 cccagagaac ccaggtgta caccctgcct cccagccagg aagagatgac caagaaccag    1020
gtgtccctga cctgcctggt gaaaggcttc taccccagcg acatcgccgt ggagtgggaa   1080
agcaacggcc agcccgagaa caattacaag acaaccccctc ccgtgctgga tagcgatggc   1140
agcttctttc tgtacagcag actgaccgtg gacaagagca gatggcagga aggcaacgtg    1200
ttcagctgca gcgtgatgca cgaagccctg cacaaccact acacccagaa gagcctgtcc    1260
ctgagcctgg gcaag                                                     1275
```

<210> SEQ ID NO 38
<211> LENGTH: 1275
<212> TYPE: DNA
<213> ORGANISM: Artificial Sequence
<220> FEATURE:
<223> OTHER INFORMATION: nucleotide sequence of modified IL-7(MGM) fused hyFc

<400> SEQUENCE: 38

```
atgttccacg tgagcttcag gtacatcttc ggcctgccac ccctgatcct ggtgctgctg       60
cctgtggcca gctccatggg gatggactgc gacatcgagg gaaaagacgg caagcagtac     120
gaaagcgtgc tgatggtgtc catcgaccag ctgctggatt ctatgaagga gattgggagt     180
aactgcctga caatgagtt caacttcttc aaacggcaca tttgtgatgc caacaaggag      240
ggaatgttcc tgtttcgggc cgctagaaaa ctgaggcagt tcctgaagat gaacagcacc    300
ggagactttg atctgcatct gctgaaagtg tctgagggca ccacaatcct gctgaactgc    360
actgggcagt gaaaggaag gaagcctgcc gctctgggag aggctcagcc aaccaagtca    420
ctggaggaaa caaaagcct gaaggaacag aagaaactga atgacctgtg ctttctgaaa    480
cggctgctgc aggagatcaa acatgttgg aacaagattc tgatgggcac aaaggaacac    540
cgcaatactg gcggggcgg ggaggaaaag aaaaaggaga aggaaaagga ggaacaggag    600
gaaagagaga ctaagacccc agaatgtccc agccatactc agcccctggg ggtgttcctg   660 tttccccta aacctaagga tacctgatg atcagcagga cacccgaggt gacctgcgtg     720
gtcgtggatg tgagccagga agatcccgaa gtgcagttca actggtacgt ggatggcgtg    780
gaagtgcaca cgccaagac caagcccaga gaagagcagt tcaactccac ctacagagtg     840
gtgagcgtgc tgaccgtgct gcaccaggac tggctgaacg gcaaggagta caagtgcaag    900
gtgtccaaca aggcctgcc cagctccatc gagaagacca tcagcaaagc caaggccag     960 cccagagaac ccaggtgta caccctgcct cccagccagg aagagatgac caagaaccag    1020
gtgtccctga cctgcctggt gaaaggcttc taccccagcg acatcgccgt ggagtgggaa   1080
```

```
agcaacggcc agcccgagaa caattacaag acaacccctc ccgtgctgga tagcgatggc    1140
agcttctttc tgtacagcag actgaccgtg gacaagagcg atggcagga aggcaacgtg    1200 ttcagctgca gcgtgatgca cgaagccctg cacaaccact acacccagaa gagcctgtcc    1260
ctgagcctgg gcaag                                                    1275
```

<210> SEQ ID NO 39
<211> LENGTH: 1278
<212> TYPE: DNA
<213> ORGANISM: Artificial Sequence
<220> FEATURE:
<223> OTHER INFORMATION: nucleotide sequence of modified IL-7(MMMM) fused hyFc

<400> SEQUENCE: 39

```
atgttccacg tgagcttcag atacatcttc ggcctgcccc ccctgatcct ggtgctgctg     60
cccgtggcca gcagcatgat gatgatggac tgcgacatcg agggcaagga cggcaagcag    120
tacgagagcg tgctgatggt gagcatcgac cagctgctgg acagcatgaa ggagatcggc    180
agcaactgcc tgaacaacga gttcaacttc ttcaagagac acatctgcga cgccaacaag    240
gagggcatgt tcctgttcag agccgccaga aagctgagac agttcctgaa gatgaacagc    300
accggcgact tcgacctgca cctgctgaag gtgagcgagg gcacaaccat cctgctgaac    360
tgcaccggcc aggtgaaggg cagaaagccc gccgccctgg gcgaggccca gcccaccaag    420
agcctggagg agaacaagag cctgaaggag cagaagaagc tgaacgacct gtgcttcctg    480
aagagactgc tgcaggagat caagacctgc tggaacaaga tcctgatggg caccaaggag    540
cacaggaaca caggcagagg cggcgaggag aagaagaagg agaaggagaa ggaggagcag    600
gaggaaagag agaccaagac ccccgagtgc cccagccaca cccagcccct gggcgtgttc    660
ctgttccctc ccaagcccaa ggacaccctg atgatcagca gaacccccga ggtgacctgc    720
gtggtcgtgg atgtgagcca ggaagatccc gaagtgcagt tcaactggta cgtggatggc    780
gtggaagtgc acaacgccaa gaccaagccc agagaagagc agttcaactc cacctacaga    840
gtggtgagcg tgctgaccgt gctgcaccag gactggctga acggcaagga gtacaagtgc    900
aaggtgtcca acaaaggcct gcccagctcc atcgagaaga ccatcagcaa agccaaaggc    960
cagcccagag aaccccaggt gtacaccctg cctccagcc aggaagagat gaccaagaac    1020
caggtgtccc tgacctgcct ggtgaaaggc ttctacccca gcgacatcgc cgtggagtgg    1080
gaaagcaacg gccagcccga gaacaattac aagacaaccc ctcccgtgct ggatagcgat    1140
ggcagcttct ttctgtacag cagactgacc gtggacaaga gcagatggca ggaaggcaac    1200
gtgttcagct gcagcgtgat gcacgaagcc ctgcacaacc actacaccca gaagagcctg    1260
tccctgagcc tgggcaag                                                  1278
```

<210> SEQ ID NO 40
<211> LENGTH: 4
<212> TYPE: PRT
<213> ORGANISM: Artificial Sequence
<220> FEATURE:
<223> OTHER INFORMATION: oligopeptides conjugated with IL-7

<400> SEQUENCE: 40

Met Met Met Met
1